(12) United States Patent
Chang et al.

(10) Patent No.: US 10,844,431 B2
(45) Date of Patent: Nov. 24, 2020

(54) NANOFLUIDIC CHANNEL OPENING SIZE CONTROL USING ACTUATION

(71) Applicant: SEAGATE TECHNOLOGY LLC, Cupertino, CA (US)

(72) Inventors: Thomas Young Chang, Menlo Park, CA (US); Kim Yang Lee, Fremont, CA (US); David S. Kuo, Palo Alto, CA (US); Erik J. Hutchinson, Eden Prairie, MN (US)

(73) Assignee: SEAGATE TECHNOLOGY LLC, Fremont, CA (US)

( * ) Notice: Subject to any disclaimer, the term of this patent is extended or adjusted under 35 U.S.C. 154(b) by 267 days.

(21) Appl. No.: 15/886,483

(22) Filed: Feb. 1, 2018

(65) Prior Publication Data
US 2018/0223354 A1   Aug. 9, 2018

Related U.S. Application Data

(60) Provisional application No. 62/453,398, filed on Feb. 1, 2017.

(51) Int. Cl.
| | |
|---|---|
| *G01N 27/447* | (2006.01) |
| *G01N 33/487* | (2006.01) |
| *B01L 3/00* | (2006.01) |
| *C12Q 1/6869* | (2018.01) |

(52) U.S. Cl.
CPC ...... *C12Q 1/6869* (2013.01); *B01L 3/502715* (2013.01); *B01L 3/502761* (2013.01); *G01N 27/44791* (2013.01); *G01N 33/48721* (2013.01); *B01L 2200/0663* (2013.01); *B01L 2200/12* (2013.01); *B01L 2300/0645* (2013.01); *B01L 2300/0896* (2013.01)

(58) Field of Classification Search
CPC .. C12Q 1/6813; C12Q 1/6876; C12Q 1/6825; C12Q 1/6869; C12Q 1/68; G01N 27/44791; G01N 27/4473; G01N 33/48721; G01N 33/48728; Y10S 977/852; Y10S 977/733; Y10S 977/72; Y10S 977/721

See application file for complete search history.

(56) References Cited

U.S. PATENT DOCUMENTS

| | | | |
|---|---|---|---|
| 9,410,923 B2 | 8/2016 | Sauer et al. | |
| 2016/0319342 A1* | 11/2016 | Kawai | C12Q 1/6869 |
| 2017/0146510 A1* | 5/2017 | Ikeda | G01N 33/48721 |

OTHER PUBLICATIONS

Di Ventra, Massimiliano, et al., "Decoding DNA, RNA and peptides with quantum tunneling," Nature Nanotechnology, vol. 11, Feb. 2016, pp. 117-126.

Feng, Yanxiao, et al., "Nanopore-based Fourth-generation DNA Sequencing Technology," Genomics Proteomics Bioinformatics, 13 (2015), pp. 4-16.

(Continued)

*Primary Examiner* — Gurpreet Kaur
(74) *Attorney, Agent, or Firm* — Holzer Patel Drennan

(57) ABSTRACT

Apparatus and methods to a DNA sequencing device and related methods that includes a substrate, a nanochannel formed in the substrate, a first electrode, a second electrode arranged opposite the first electrode, a distance between the first and second electrodes defining an electrode gap that is exposed within the nanochannel, and at least one actuator operable to move at least one of the first and second electrodes to adjust a size of the electrode gap.

19 Claims, 16 Drawing Sheets

(56) References Cited

OTHER PUBLICATIONS

Ivanov, A.P., et al., "DNA Tunneling Detector Embedded in a Nanopore," Nano Letters, 2011, 11, pp. 279-285.

Ke, Rongqin, et al., "Fourth Generation of Next-Generation Sequencing Technologies: Promise and Consequences," Human Mutation, vol. 37, No. 12, 2016, pp. 1363-1367.

Kulski, Jerzy K., "Next-Generation Sequencing—An Overview of the History, Tools, and 'Omic' Applications," http://dx.doi.org/10.5772/61964, 59 pages.

* cited by examiner

NANOFLUIDIC CHANNEL OPENING SIZE CONTROL USING ACTUATION

RELATED APPLICATIONS

This application claims the benefit of the filing date of U.S. Provisional Application No. 62/453,398, filed on 1 Feb. 2017, and entitled NANOFLUIDIC CHANNEL OPENING SIZE CONTROL USING ACTUATION, and U.S. Provisional Application No. 62/453,376, filed on 1 Feb. 2017, and entitled MICRO AND NANOFLUIDIC CHANNEL CONTROLLED ACTUATION TO OPEN CHANNEL GAP, the disclosures of which are incorporated in their entireties by this reference.

SUMMARY

The present disclosure relates to DNA sequencing device, methods of making and using DNA sequencing devices, and methods of sequencing DNA strands using a DNA sequencing device. One aspect of the present disclosure relates to a DNA sequencing device that includes a substrate, a nanochannel formed in the substrate, a first electrode, a second electrode arranged opposite the first electrode, a distance between the first and second electrodes defining an electrode gap that is exposed within the nanochannel, and at least one actuator operable to move at least one of the first and second electrodes to adjust a size of the electrode gap.

The first electrode may be arranged parallel with the nanochannel and the second electrode is arranged perpendicular to the first electrode. The second electrode may be positioned in the substrate. The size of the electrode gap after adjustment by the at least one actuator may be in the range of about 0.3 nm to about 2 nm. The at least one actuator may include at least one of a heating element, a piezoelectric or piezoceramic material, a cooling element, and an electrostatic member. The at least one actuator may include first and second actuators operable to separately move the first and second electrodes, respectively. The device may include a thermal conductor layer positioned in the substrate between the at least one actuator and at least one of the first and second electrodes. The at least one actuator may be embedded in the substrate. The device may include a plurality of first electrodes and a plurality of second electrodes arranged to provide a plurality of electrode gaps that are each exposed within the nanochannel, and the at least one actuator may be operable to move at least one of the plurality of first electrodes and the plurality of second electrodes to adjust the size of the plurality of electrode gaps.

Another aspect of the present disclosure relates to a method of forming a DNA sequencing device. The method includes forming a nanochannel in a substrate, positioning a first electrode in the substrate, positioning a second electrode spaced apart from the first electrode to form an electrode gap, the electrode gap being exposed in the nanochannel, and operating at least one actuator to move at least one of the first and second electrodes to adjust a size of the electrode gap.

The method may also include positioning the at least one actuator in the substrate. The method may include positioning a thermal conductor layer between the at least one actuator and at least one of the first and second electrodes. The at least one actuator may be one of a heating element, a piezoelectric or piezoceramic material, a cooling element, and an electrostatic member. The at least one actuator may include first and second actuators operable to separately move the first and second electrodes, respectively. The method may include providing a plurality of first electrodes and a plurality of second electrodes arranged to provide a plurality of electrode gaps that are each exposed within the nanochannel, and operating the at least one actuator may move at least one of the plurality of first electrodes and the plurality of second electrodes to adjust a size of the plurality of electrode gaps. The at least one actuator may include a separate actuator operable to move each of the first and second electrodes separately.

A further aspect of the present disclosure relates to a method of DNA sequencing. The method includes providing a DNA sequencing device having a nanochannel, first and second electrodes, and at least one actuator, a spacing between the first and second electrodes defining an electrode gap, and the electrode gap being exposed in the nanochannel. The method also includes operating the at least one actuator to move at least one of the first and second electrodes to adjust a size of the electrode gap, passing a DNA strand through the electrode gap, and detecting a change in electronic signal as the DNA strand passes through the electrode gap. The detected change in electronic signal may be associated with one or more individual nucleotides of the DNA strand. The change in electronic signal may be used to determine a sequence of the nucleotides for the DNA strand.

The at least one actuator may be fixed to a substrate, and the nanochannel may be formed at least in part in the substrate. The electrode gap may initially be closed, and operating the at least one actuator may move the first and second electrodes away from each other to a provide a size for the electrode gap in the range of about 0.3 nm to about 2 nm. The electrode gap may initially be greater than 2 nm, and operating the at least one actuator may move the first and second electrodes toward each other to a provide a size for the electrode gap in the range of about 0.3 nm to about 2 nm.

The foregoing has outlined rather broadly the features and technical advantages of examples according to this disclosure so that the following detailed description may be better understood. Additional features and advantages will be described below. The conception and specific examples disclosed may be readily utilized as a basis for modifying or designing other structures for carrying out the same purposes of the present disclosure. Such equivalent constructions do not depart from the scope of the appended claims. Characteristics of the concepts disclosed herein, including their organization and method of operation, together with associated advantages will be better understood from the following description when considered in connection with the accompanying figures. Each of the figures is provided for the purpose of illustration and description only, and not as a definition of the limits of the claims.

BRIEF DESCRIPTION OF THE DRAWINGS

A further understanding of the nature and advantages of the present disclosure may be realized by reference to the following drawings. In the appended figures, similar components or features may have the same reference label. Further, various components of the same type may be distinguished by following a first reference label with a dash and a second label that may distinguish among the similar components. However, features discussed for various components, including those having a dash and a second reference label, apply to other similar components. If only the first reference label is used in the specification, the description is applicable to any one of the similar components having the same first reference label irrespective of the second reference label.

DETAILED DESCRIPTION

Figure 1:
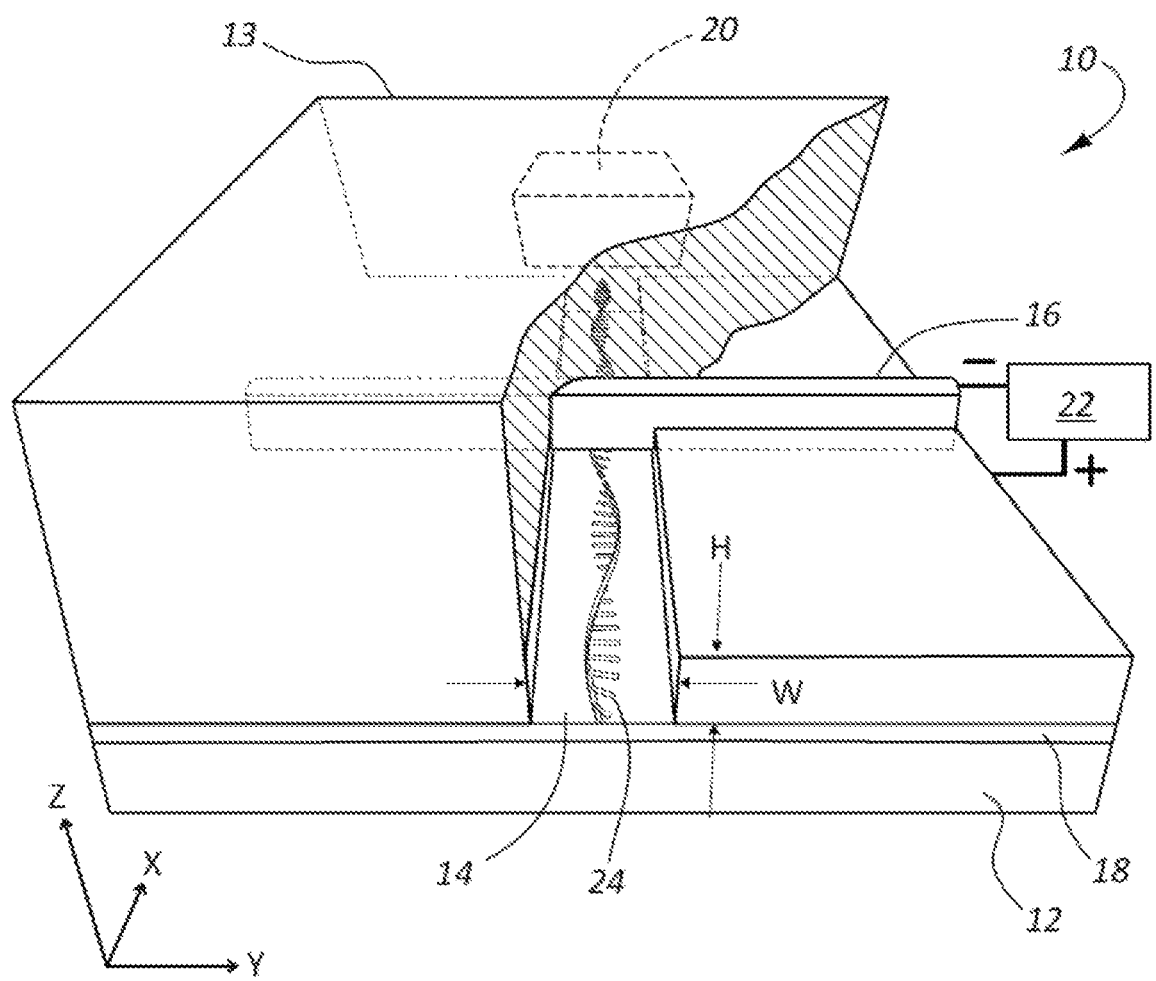
FIG. 1 schematically illustrates an example DNA sequencing device with a tunneling electrode having a heater actuator operable to move the electrodes towards each other to adjust an electrode gap size in accordance with the present disclosure.

Despite considerable efforts, DNA sequencing today still suffers from high costs and low speeds. To address these issues, various methods have been proposed over the past decade that would allow individual DNA strands to be read directly. Among these, nanopore- and nanochannel-based approaches have emerged as the most promising. However, many challenges exist related to fabricating a channel and/or pore opening that is sufficiently small to limit passage to a single DNA strand, and there is no relatively mature method that addresses this unmet need.

Direct DNA sequencing has drawn attention due to its advantages on long read length, high throughput and low cost. Direct DNA sequencing methods using transverse tunneling current measurement have been studied extensively in literature. However, a manufacturably viable direct DNA sequencing device with required dimensions for the gap between the nanoelectrodes, nor methods for creating such a device, have not been discovered. Conventional MEMS and nanofabrication methods are inadequate for creating the required structure.

Direct measure of individual nucleotides of long DNA strands rapidly and with low cost is one of the goals of many DNA sequencing devices and methods. Among these, nanopore- and nanochannel-based approaches that measure a transverse signal across individual nucleotides of the DNA strand have emerged as a promising approach. The general approach involves electrically driving DNA and RNA strands through a nanopore or narrow nanochannel via ionic flow or driven by a pressure gradient.

As the DNA strands pass a high resolution sensor embedded inside the nanochannel, the high spacial resolution sensor measures the unique properties of the individual nucleotides (A,T,C,G). One type of sensor may include a conductive electrode or sensor that measures the unique tunneling currents of the nucleotides thereby identifying and resolving the four unique nucleotide types. However, there are several significant challenges associated with the fabrication of such devices, particularly at low cost, that can spacially resolve individual nucleotides in a DNA strand, which are on the order of 1 nm is size in a transverse direction.

A first of these challenges includes the ability to fabricate a nanochannel width on the order of about 1 nm (e.g., in the range of about 0.1 nm to about 5 nm, and more particularly about 0.3 nm to about 2 nm) accurately and repeatable to obtain significant tunneling current which is exponential verses distance. For example, the signal tunneling current may reduce by a factor of 1000× if spacing is increased between probe and base molecule by only 0.5 nm. Another challenge relates to the fabrication of a sensor (e.g., an electrode gap) having no more than about 0.3 nm to about 2 nm in width in order to resolve and detect individual nucleotides in the DNA strand.

One aspect of the present disclosure relates to a DNA sequencing device and related methods that provide control of a dimension of the nanochannel (e.g., a width or height), and/or a dimension of a spacing or gap between electrode members of the nanoelectrode that are exposed within the nanochannel. The size adjustment for the nanochannel and/or nanoelectrode gap (also referred to as an electrode gap, sensor gap, or gap) may be carried out using mechanical actuation rather than by lithography and/or layer thickness. The mechanical actuation may be used to set a dimension of the nanochannel and/or a final or any intermediate size for the electrode gap. Deactivation of the actuator may permit the actuated feature (e.g., nanochannel dimension or electrode gap size) to return to an initial or rest state. The mechanical actuator may provide Angstrom level precision control when activated. This Angstrom level control may help achieve, for example, high tunneling current signal-to-noise ratio (SNR) used to distinguish specific nucleotides (A,T,G,C) of the DNA strand.

The present disclosure may provide direct measure of individual nucleotides of DNA strands relatively rapidly and with relatively low cost. A device that can measure a localized transverse tunneling signal across individual nucleotides may provide a number of advantages. One challenge related to such devices is that such devices require the DNA to pass through a nanochannel opening (e.g., an electrode gap within the nanochannel) on the order of about 0.3 nm to 2 nm, and typically with Angstrom level control. Another challenge is the need to fabricate a conductive probe within this nanochannel opening with a relatively short range apex dimension on the order of about 1 nm.

The present disclosure provides, in at least one embodiment, an actuator (e.g., active element) positioned in the device (e.g., relatively close to the nanochannel and nanoelectrode) that operates to adjust a dimension of the nanochannel or electrode gap. In one embodiment, the actuator is at least partially embedded in a layer of the device. The actuator, when activated, may either push or pull (e.g., expand and/or contract) the material in the region surrounding the electrode thereby causing mechanical displacement of some aspect of the structure (e.g., wall of the nanochannel or one or more of the electrode members of the nanoelectrode). One or more of the electrode elements of the nanoelectrode may be mounted to the moving nanochannel wall(s), thereby changing, for example, the gap between the electrode members. The amount of energy put into the actuator may control the magnitude of the displacement. Thus, the nanochannel dimension (e.g., gap between electrode elements within the nanochannel) can be controlled to any desired size and controlled within, for example, Angstroms of spacing.

FIG. 1 schematically illustrates a transverse DNA sequencing device 10 having at least one feature that provides size adjustments for a tunneling electrode gap G. The device 10 includes a nanochannel 14 formed in a substrate 12. The nanochannel 14 is represented by the open space within the device 10 along the length of the device 10. The nanochannel allows a DNA strand 24 to flow through the device 10 and past the pair of sensing electrodes 16, 18, which are positioned at a location along the nanochannel 14 in the X direction.

The nanochannel height is represented by H. The dimension G represents the narrowest opening within the nanochannel, which is typically at the location of the sensing electrodes 16, 18. In operation, the DNA strand 24 is pushed along this nanochannel 14 by either ionic flow or pressure gradient along the X direction. As the DNA strand passes the electrodes 16, 18, the tunneling current is measured (e.g., using a controller or pre-amp 22, which is electrically connected to the electrodes 16, 18) and its magnitude will change corresponding to the specific nucleotide (e.g., A,T, C,G) of the DNA strand passing between electrode members 16, 18 at a given time. Controlling the nanochannel dimension G is one focus of the present disclosure. Because the tunneling current that is typically on the order of pecofarads and is exponential in nature vs. distance G, the dimensional control of the nanochannel size typically is on the order of Angstroms. For example, 1 Angstrom change in G will result in roughly 10× change in tunneling current, and 3 Angstrom change in G will result in roughly 1000× change in tunneling current.

Figure 2:
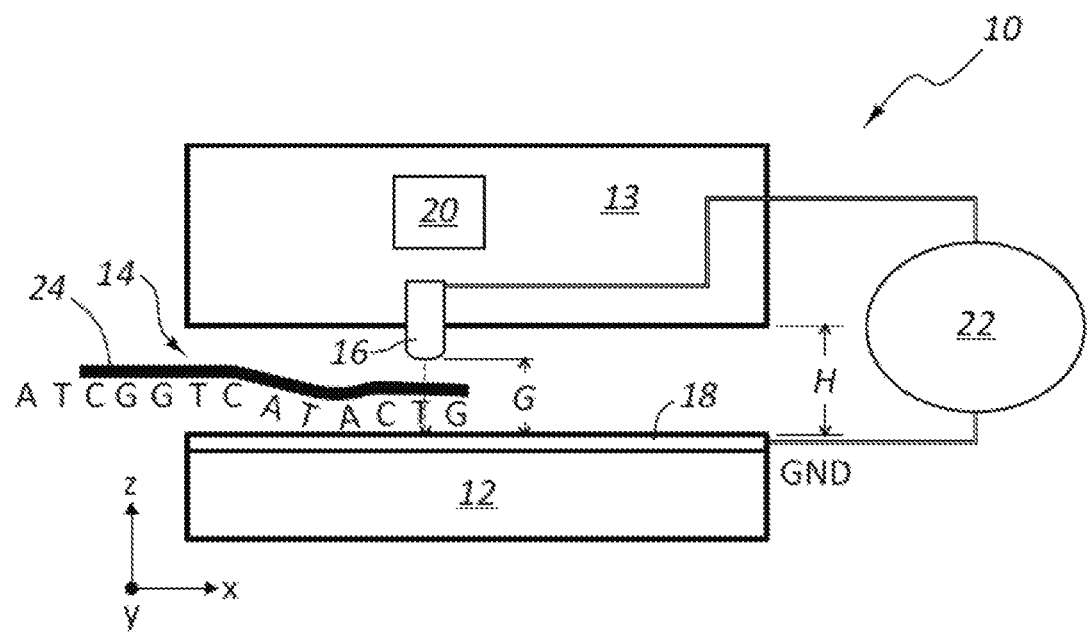
FIG. 2 is a cross-sectional view of the DNA sequencing device shown in FIG. 1.
Figure 3A:
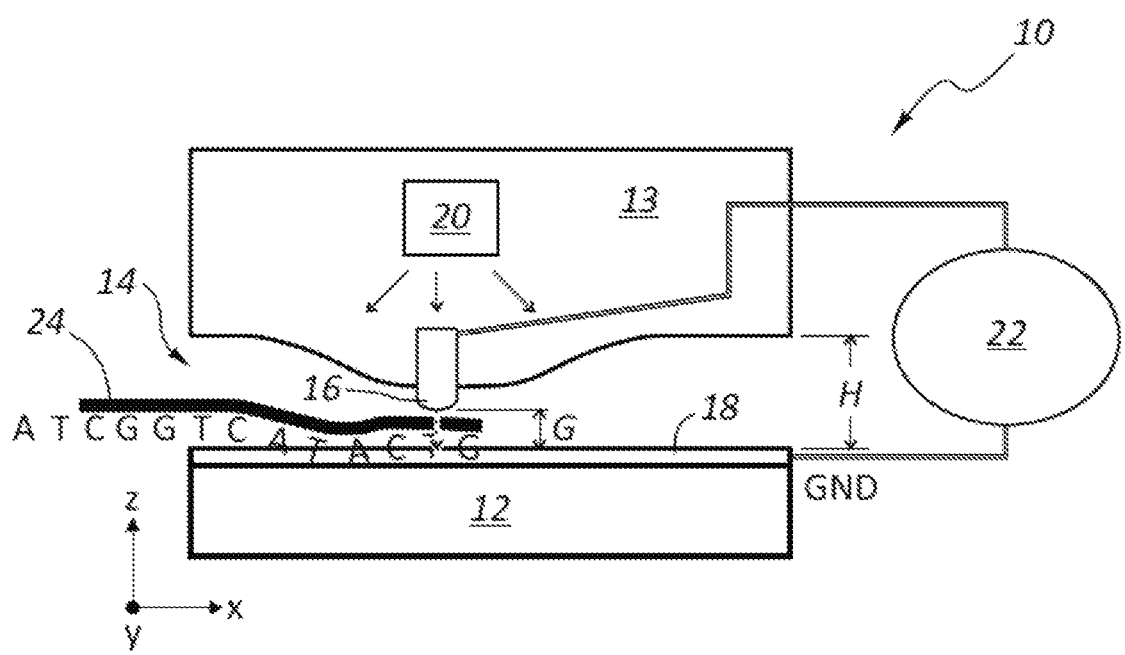
FIGS. 3A-3B schematically illustrate the DNA sequencing device of FIG. 2 with the actuator activated to move the electrodes towards each other.
Figure 3B:
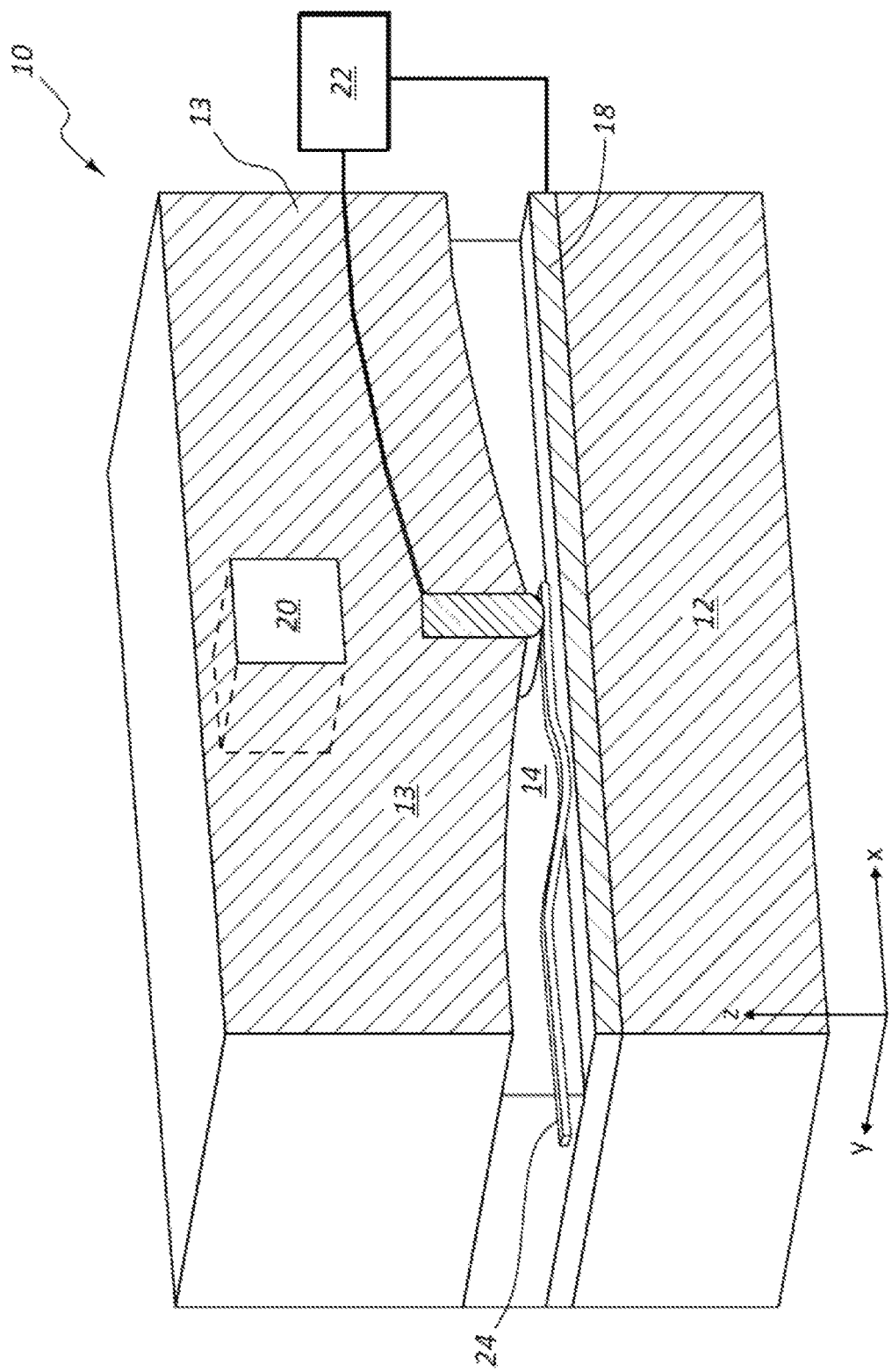

As mentioned above, the critical dimensions G is typically difficult to fabricate on the order of 0.3 nm to 2 nm and with Angstrom level tolerances. The use of active spacing control to position the electrode to the required spacing can provide advantages related to these challenges. FIGS. 1-3B illustrate an active element or actuator 20, which when turned on, causes a net displacement of the electrode 16 along the z direction, thereby allowing more precise spacing control of the nanochannel dimension G. FIGS. 1 and 2 illustrate the device in the OFF state. FIGS. 3A-3B illustrate the device 10 in the ON state in which the actuator 20 is activated to cause a displacement of at least one of the electrode members 16, 18 and reduce the dimension G.

In the embodiment of FIGS. 1-3B, the actuator 20 may be a resistive element and may be referred to as a heater actuator. In the ON state, a current is applied to the actuator 20, thereby causing heating of the actuator 20, which in turn expands the material 13 surround the actuator 20. The expansion of material 13 physically moves the electrode 16 along the Z direction causing a narrowing of the gap G in the nanochannel 14. In some embodiments, heat may first be applied to achieve contact between the electrode members 16, 18 to set a reference position. Then current delivered to the actuator 20 is reduced, which results in the electrode member 16 to pulling back relative to the electrode member 18 to achieve a final nanochannel restriction spacing, G. FIG. 3B shows a perspective of the electrode members to visualize the connection along the Z direction.

The actuator 20 may operate to move the electrode 16 a distance in the range of about 5 nm to about 20 nm, and more particularly about 10 nm. Typically, the nanochannel dimension H is greater than the maximum distance the electrode 16 can be moved by operation of the actuator 20.

The actuator 20 may comprise a conductive material having properties such as, for example, high resistance and high melting temperature. Some example materials include nickel chromium (NiCr) and tungsten (W).

Figure 4A:
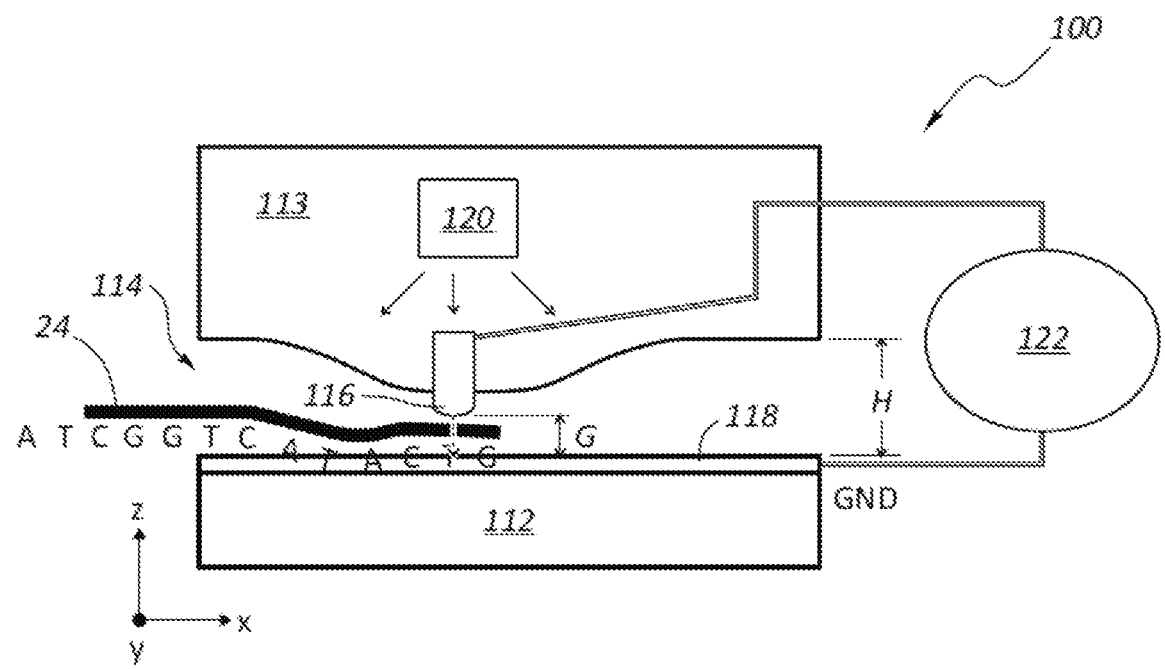
FIG. 4A schematically illustrates an example DNA sequencing device with a tunneling electrode having a piezoelectric/piezoceramic actuator operable to move the electrodes towards each other to adjust an electrode gap size in accordance with the present disclosure.
Figure 4B:
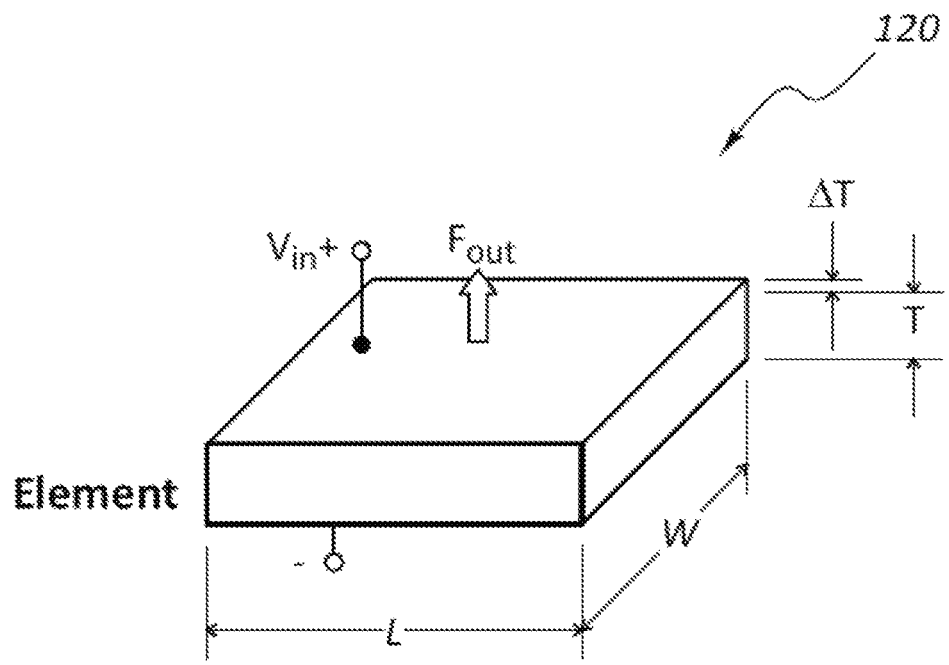
FIG. 4B schematically illustrates the piezoelectric/piezoceramic actuator of FIG. 4A.

FIGS. 4A and 4B illustrate a second DNA sequencing device 100 embodiment in which an actuator 120 comprises a piezoelectric/piezoceramic material. When a voltage is applied across the actuator 120, and electric field is formed across the thickness of a sheet of piezoceramic material, and the material of the actuator 120 expands in thickness. This expansion cause the material 113 surrounding the actuator 120 to also expand. As a result, the electrode member 116, which may be mounted to the material 113 or embedded in the material 113 beneath the actuator 120 will be pressed towards the ground electrode member 118 and a reduction in the gap G between the electrode members 116, 118 will occur in the nanochannel 114 to obtain a desired gap G. The change in gap G will influence the tunneling current measured by the electrode members 116, 118 (e.g., using a controller or pre-amp 122).

For actuation using the piezoelectric/piezoceramic materials of FIGS. 4A-4B, the device 100 typically uses a low current high voltage DC. Depending on the amount of actuation in nm, and the configuration of the piezo device, the voltage in one example may be in the range of about 10 V to about 1000 V. The range of voltage can be signification because of piezo device can be configured many ways. If more force and range are required, the amount of voltage can be increased within the disclosed range.

FIG. 4B illustrates an example actuator 120 that includes piezoelectric/piezoceramic materials. The actuator 120 may have a length L, a width W, and a thickness T. The thickness T may change by an amount $\Delta T$ when the actuator 120 is activated. This change in $\Delta T$ may create a force $F_{out}$ that is used to move the electrode 116.

Figure 5:
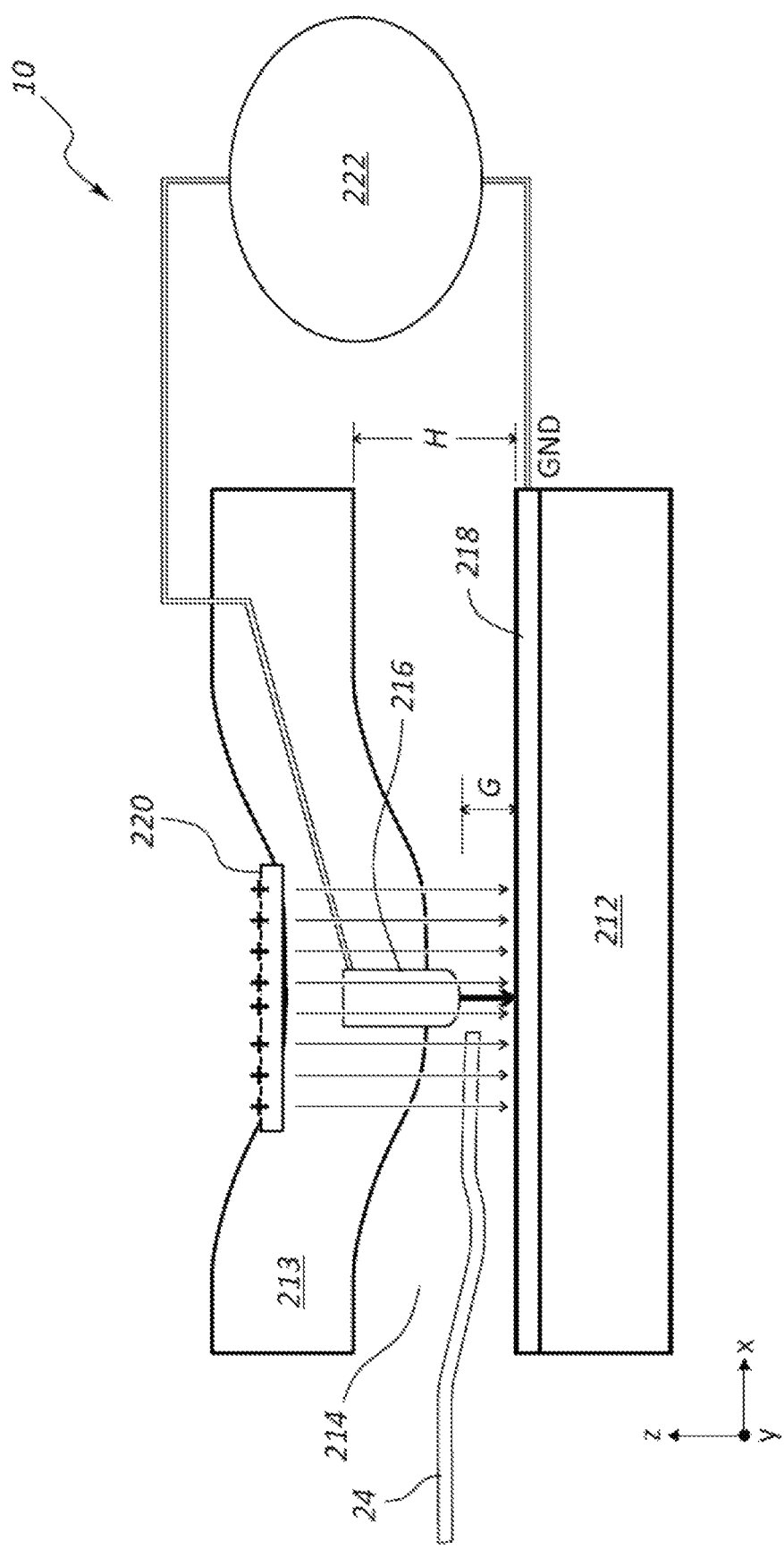
FIG. 5 schematically illustrates an example DNA sequencing device with a tunneling electrode having an electrostatic actuator operable to move the electrodes towards each other to adjust an electrode gap size in accordance with the present disclosure.

FIG. 5 shows another embodiment of a DNA sequencing device 200 in which an actuator 220 operates by electrostatic force with a compliant beam structure in order to move one of the electrode members 216, 218. The application of an electric field via the actuator 220 within the material 213 causes an attractive force between top and bottom electrode members 216, 218. The device 200 may include a beam structure to which at least one of the electrode members 216, 218 is mounted. The beam structure may facilitate movement of the electrode member 216 toward the electrode member 218 (e.g., ground electrode) to achieve a desired gap G within the nanochannel 214. The change in gap G will influence the tunneling current measured by the electrode members 216, 218 (e.g., using a controller or pre-amp 222).

The amount of energy needed to operate the actuator 220 of device 200 may vary depending on a number of factors and properties of the device 200. In a capacitive actuator, the current may be close to zero in some embodiments, with voltage in the range of about 1 V to about 100 V. The actuation force may be limited and may be less than the piezo and heater actuators described above. The actuator 220 may comprise parallel conductive plates.

One option for the material of the beam structure may include a polymer material, which may provide relatively high mechanical compliance as compared to other available materials and/or materials that form other portions of the DNA sequencing device 200. This compliance may allow the beam structure to bend with minimum amount of force provided by the attractive electric field provided by actuator 220. Further, when the electric field is turned OFF, the beam will more easily return to its original state/form (e.g., straight).

FIGS. 6A-6D show various electrode embodiments for use with the active element features of DNA sequencing device. The bottom or ground electrode may be positioned on the side of the nanochannel adjacent to the actuator, or be positioned on an opposite side of the nanochannel at a location spaced away from the actuator. The electrode members have be formed as a layer or have a probe structure. The probe structure may have a tapered and/or pointed tip that is exposed in the nanochannel. Some embodiments include a plurality of electrode pairs exposed within a single nanochannel at spaced apart locations along the nanochannel. A separate actuator may be used to control the position of each electrode member individually, or a separate actuator may be used for each electrode pair.

Figure 6A:
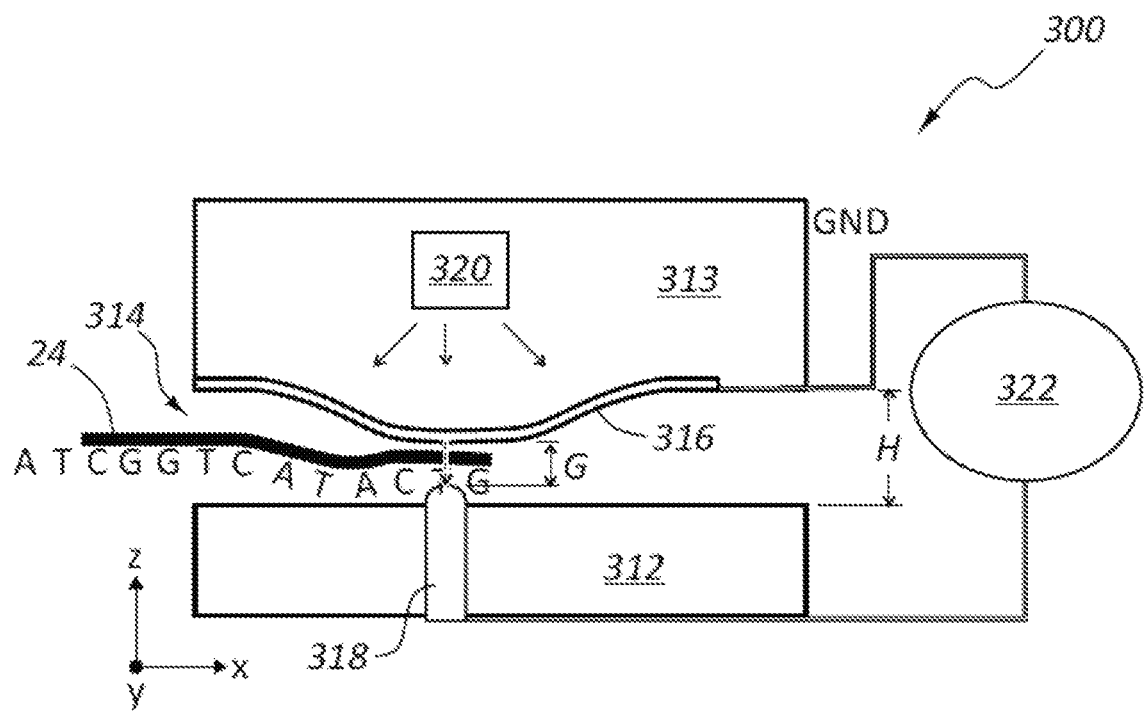
FIGS. 6A-6D schematically illustrate example DNA sequencing devices with various electrode embodiments in accordance with the present disclosure.

FIG. 6A illustrates a DNA sequencing device 300 that includes a heat activated actuator 320 positioned in material 313 of the device 300. A first electrode member 316 is provided as a layer or plate that is positioned on a side of the nanochannel 314 adjacent to the actuator 320. The second or bottom electrode member 318 is positioned on a side of the nanochannel 314 opposite the location of the actuator 320. In the ON state, a current is applied to the actuator 320, thereby causing heating of the actuator 320, which in turn expands the material 313 surround the actuator 320. The expansion of material 313 physically moves at least portions of the electrode member 316 along the Z direction causing a narrowing of the gap G in the nanochannel 314 to a desired gap G. The change in gap G will influence the tunneling current measured by the electrode members 316, 318 (e.g., using a controller or pre-amp 322).

Figure 6B:
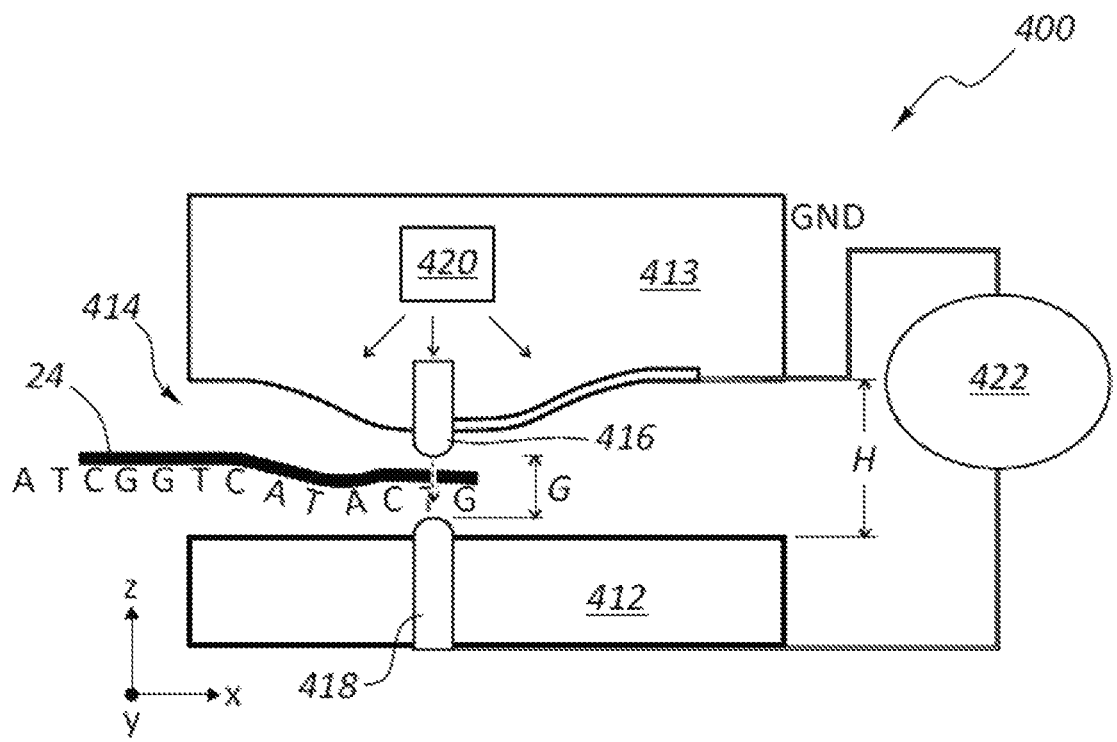

FIG. 6B illustrates a DNA sequencing device 400 that includes an actuator 420 positioned in material 413 of the device 400. A first or top electrode member 416 is provided as a probe that is positioned on a side of the nanochannel 414 adjacent to the actuator 420. The second or bottom electrode member 418 is positioned on a side of the nanochannel 414 opposite the location of the actuator 420 and also has a probe shape. In the ON state, a current is applied to the actuator 420, thereby causing heating of the actuator 420, which in turn expands the material 413 surround the actuator 420. The expansion of material 413 physically moves the electrode member 416 along the Z direction causing a narrowing of the gap G in the nanochannel 414 to a desired gap G. The change in gap G will influence the tunneling current measured by the electrode members 416, 418 (e.g., using a controller or pre-amp 422).

Figure 6C:
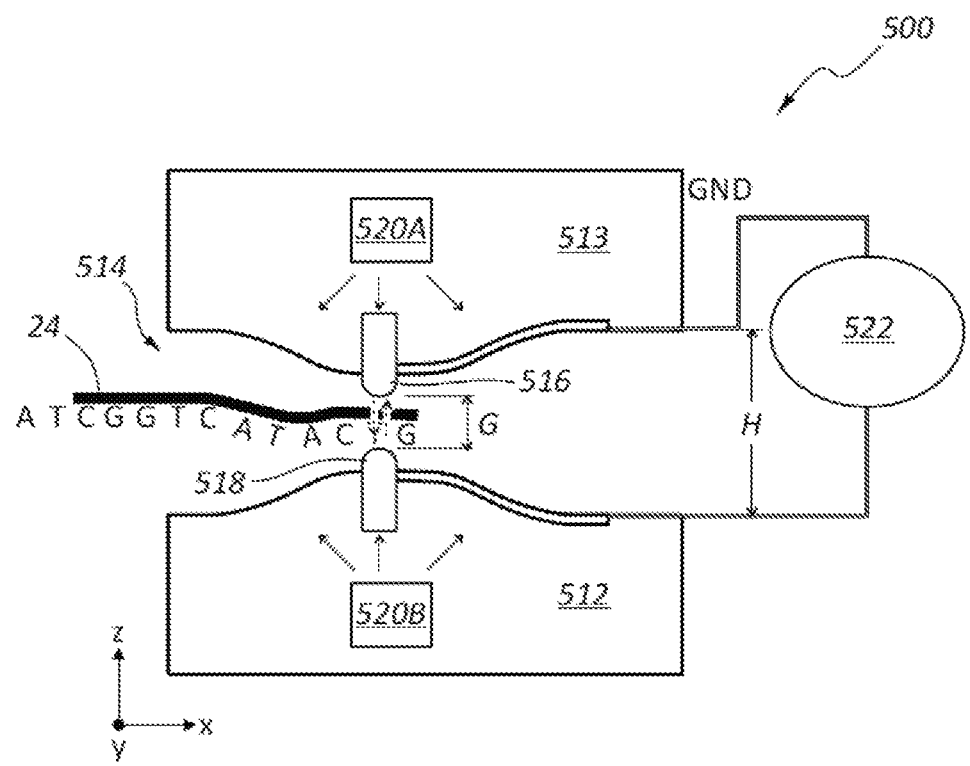

FIG. 6C illustrates a DNA sequencing device 500 that includes first and second actuators 520A, 520B positioned in material 513, 512 of the device 500, respectively. A first electrode member 516 is provided as a probe or as a layer or plate that is positioned on a side of the nanochannel 514 adjacent to the actuator 520. The second or bottom electrode member 518 is also provided as a probe or as a layer or plate that is positioned on a side of the nanochannel 514 opposite the location of the actuator 520. In the ON state, a current is applied to one or both of the actuators 520A 520B, thereby causing heating of the one or more actuators 520A, 520B, which in turn expands at least one of the materials 513, 512 that surrounds the actuators 520A, 520B. The expansion of materials 513, 512 physically moves one or both of the electrode members 516, 518, depending on which of the actuators 520A, 520B is activated, along the Z direction causing a narrowing of the gap G in the nanochannel 514 to a desired gap G. The change in gap G will influence the tunneling current measured by the electrode members 516, 518 (e.g., using a controller or pre-amp 522).

Multiple independent actuation provided by actuators 520A, 520B may add further complexity and cost to the device 500 as compared to other designs disclosed herein. However, providing multiple actuators may also increase accuracy, control, and improved signal-to-noise ratios.

Figure 6D:
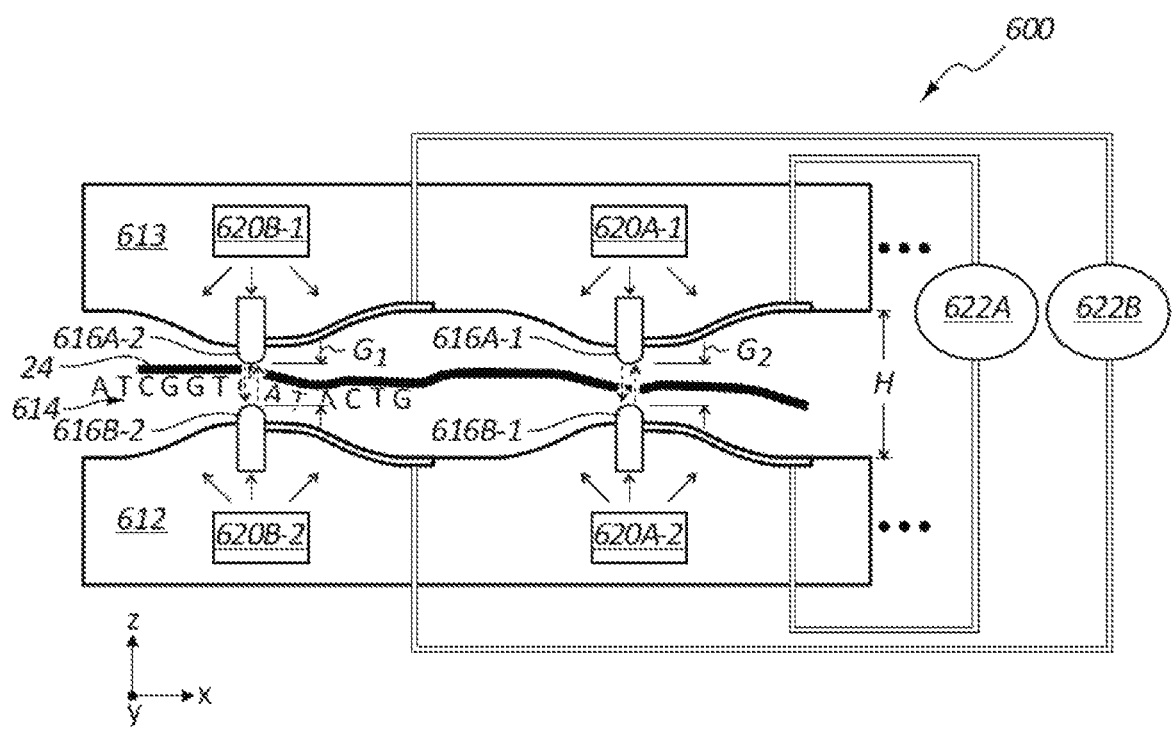

FIG. 6D illustrates a DNA sequencing device 600 that includes two pairs of electrode members 616, 618 and a separate actuator 620 for controlled movement of each of the electrode members 616, 618 individually. Electrodes 616A-1 and 616A-2 may be positioned in material 613 of the device 600 on one side of a nanochannel 614. Separate actuators 620A-1 and 620A-2 may be operable to move the electrodes 616A-1 and 616A-2. Electrodes 616B-1 and 616B-2 may be positioned in material 612 of the device 600 on an opposite side of a nanochannel 614. Separate actuators 620B-1 and 620B-2 may be operable to move the electrodes 616B-1 and 616B-2. The expansion of material 613 by operation of 620A-1 and 620A-2 may move the electrodes 616A-1, 616A-2, respectively, along the Z direction causing a narrowing of the gaps G in the nanochannel 614 to a desired gaps G. Additionally, or alternatively, expansion of material 612 by operation of 620B-1 and 620B-2 may move the electrodes 616B-1, 616B-2, respectively, along the Z direction causing a narrowing of the gaps G in the nano-channel 614 to a desired gaps G. The change in gap G will influence the tunneling current measured by the electrode members 616, 618 (e.g., using a controller or pre-amp 622).

The actuators 320, 420, 520, 620 described with reference to FIGS. 6A-6D may be any desired type of actuator (e.g., heat, piezoelectric/piezoceramic, electrostatic, etc.), such as those actuators described with reference to FIGS. 1-5. Further, while particular shapes and configurations for the electrodes are illustrated and described, such electrodes may have any desired shape, size and/or configuration.

Figure 7:
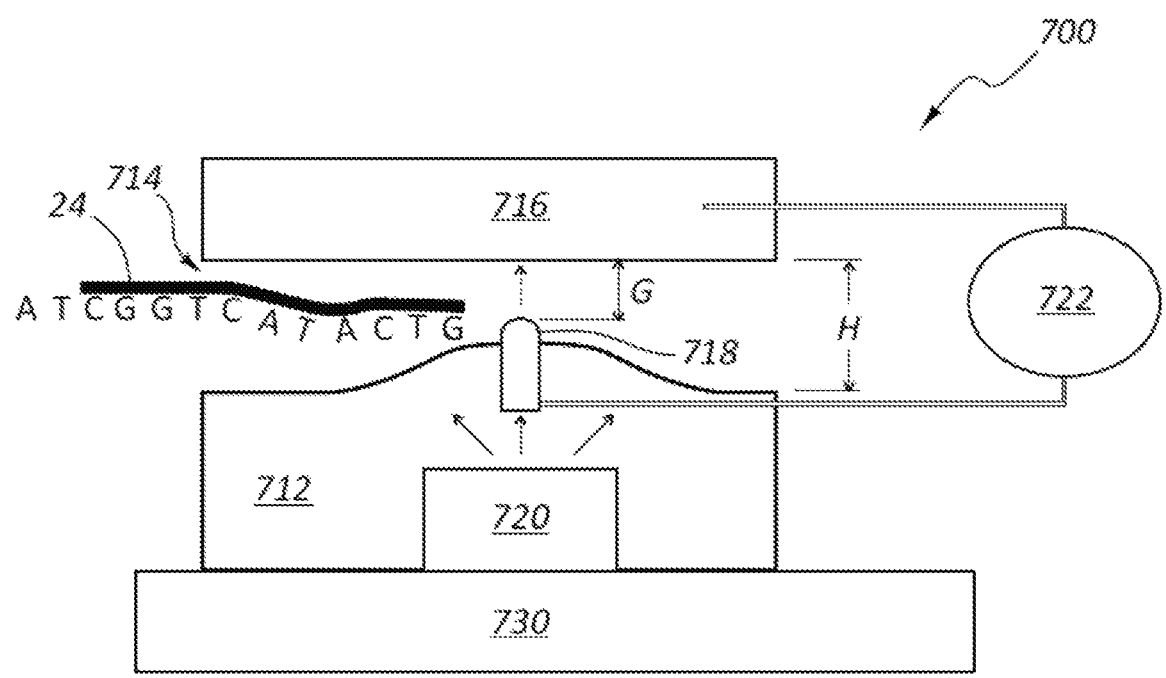
FIG. 7 schematically illustrates an example DNA sequencing devices with a heat shield in accordance with the present disclosure.

FIG. 7 schematically illustrates a DNA sequencing device 700 formed using, for example, a thin film and/or nanoimprint process. The actuator 720 may be placed in material 712. The movable electrode member 718 is also positioned in or mounted to the material 712. An opposing surface of the nanochannel 714 may include or be formed entirely from a conductive material (e.g., Tungsten (Tu) or other ground material) to provide a second electrode member 716. In some embodiments, the second electrode member 716 may be a ground electrode. Operating the actuator 720 may expand the material 712, which expansion causes the material 712 surrounding the actuator 720 to also expand. As a result, the electrode member 718 will be moved towards the electrode member 716 and a reduction in the gap G between the electrode members 716, 718 will occur in the nanochannel 714 to obtain a desired gap G. The change in gap G will influence the tunneling current measured by the electrode members 716, 718 (e.g., using a controller or pre-amp 722).

Figure 8A:
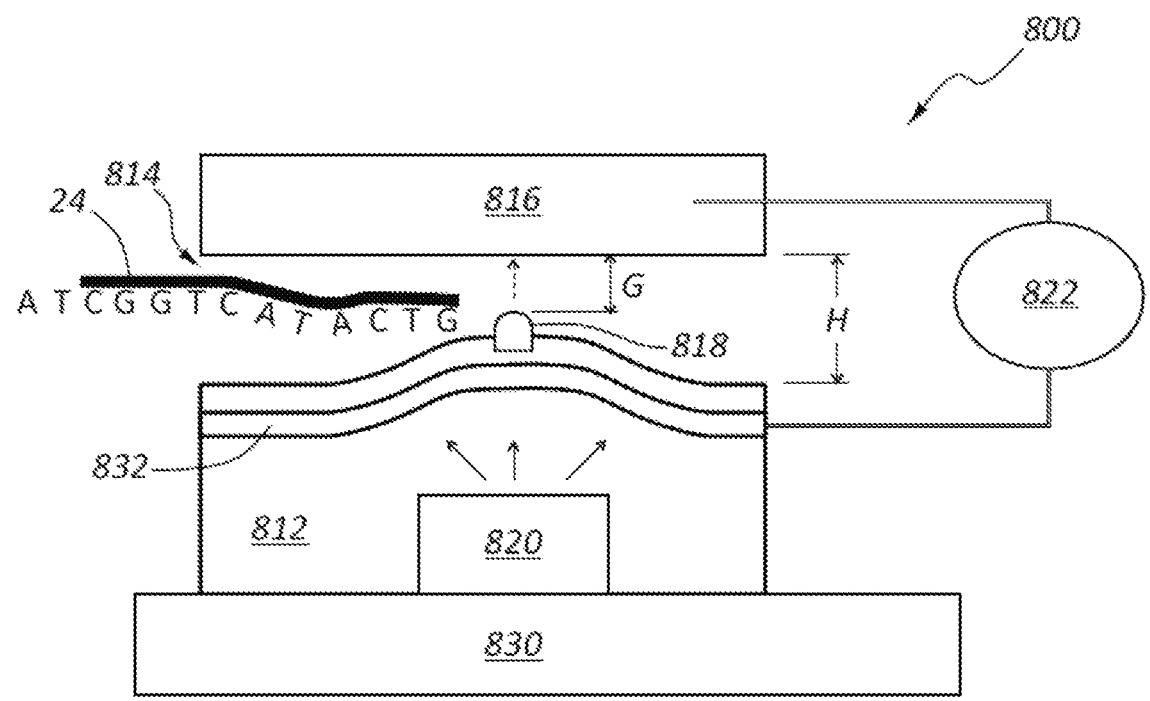
FIGS. 8A-8C schematically illustrate another example DNA sequencing devices with a heat shield in accordance with the present disclosure.
Figure 8B:
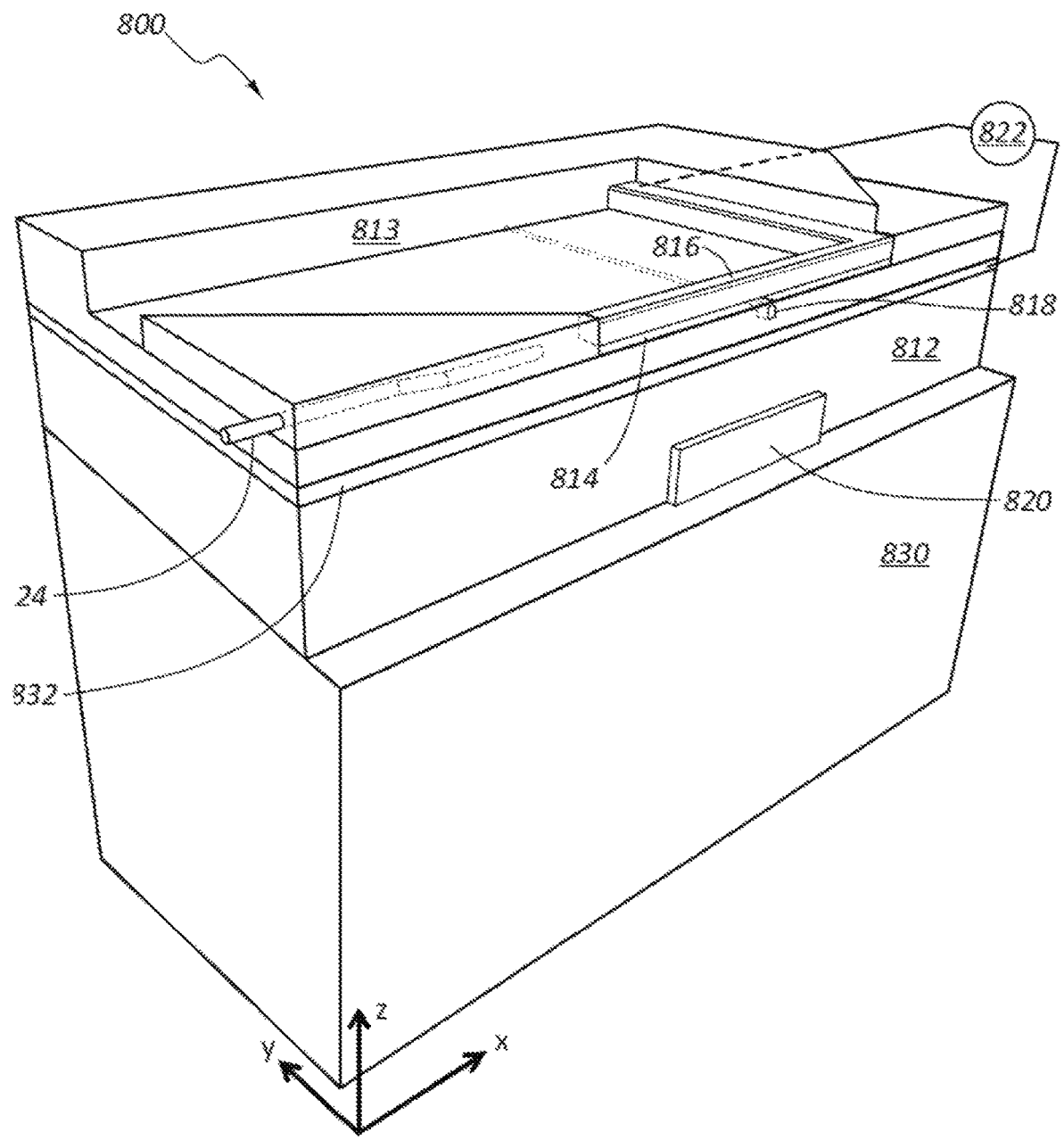
Figure 8C:
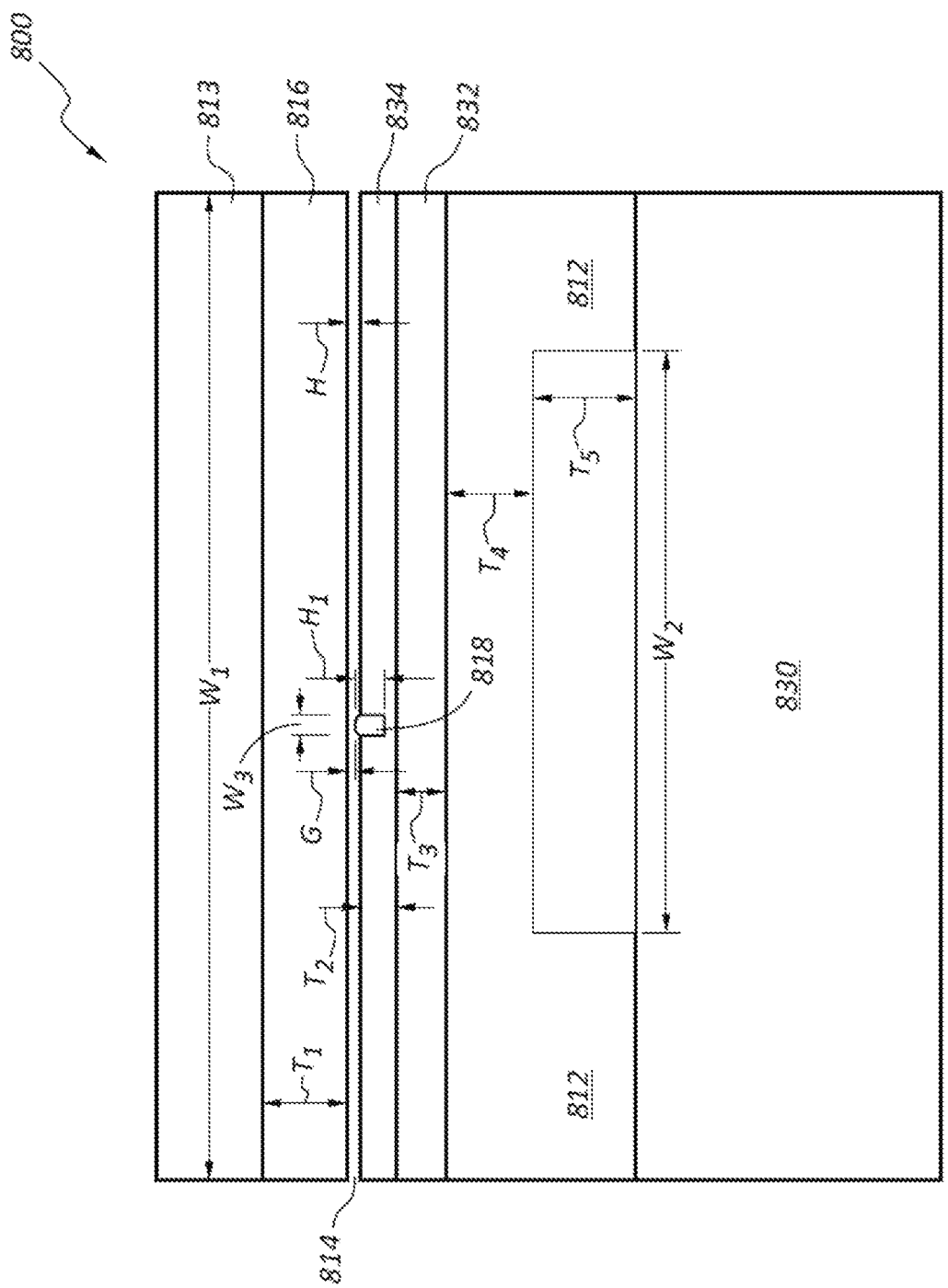

FIGS. 8A-8C show a modification to the base structure to manage heat increase within the nanochannel due to operation of the heating element. Excessive heat generated by the heating element may be detrimental to the DNA sample. A layer 832 (e.g., a heat shield, heat sink or heat dissipation member) be positioned between the actuator 820 (e.g., heating element) and the electrode member 818 to dissipate the heat before reaching the DNA sample in nanochannel 814. The layer 832 may comprise a material having low thermal conductivity, but having high thermal expansion properties. Some example materials include photo-resist materials such as essential glass that is cured.

The second or top electrode member 818 may define a surface along an entire length of the nanochannel 814, and may or may not be embedded in or mounted to a substrate material 813 (see FIG. 8B). Operating the actuator 820 may expand the material 812, which expansion causes the material 812 surrounding the actuator 820 to also expand. As a result, the electrode member 818 will be moved towards the electrode member 816 and a reduction in the gap G between the electrode members 816, 818 will occur in the nanochannel 814 to obtain a desired gap G. The change in gap G will influence the tunneling current measured by the electrode members 816, 818 (e.g., using a controller or pre-amp 822).

In some embodiments, the heating element of the actuator 820 operates at or below about 50° C., and more particularly at or below about 25° C. The material 812 surrounding or overlaying the actuator 820 may be, for example, a high thermal expansion material or a spin on glass material such as SiOx.

The heating element of the actuator 820 may be formed on, for example, glass or Silicone (Si) layer or material 830 depending on the desired heat dissipation properties, durability, and the like. In some embodiments, the DNA sequencing device 800 may be intentionally designed to wear out within a certain number of cycles of use. The device may be relatively inexpensive to manufacture and replace as compared to other more expensive electronics with which it is used.

The embodiments of FIGS. 8A-8C may include an electrode member 816 having dimensions of about 20 nm wide ($W_1$) by about 20 nm thick ($T_1$). The nanochannel 814 may have a height H of about 4 nm to about 10 nm and a width (not shown) of about 10 nm to about 30 nm. A Carbon or SiOx layer 834 (see FIG. 8C) may have a thickness $T_2$ of about 10 nm. The heat dissipation (metal) layer 832 may have a thickness $T_3$ of about 0.1 to about 0.5 µm. A spacing $T_4$ between the heat dissipation layer and the heating element may be about 1 µm±0.5 µm, although this dimension may not be critical (e.g., could be thicker or thinner). The actuator 820 may comprise NiCr or a similar material. The actuator 820 may have a thickness $T_5$ of less than about 1 µm, although a thinner structure may be easier to form. In one embodiment, the heating element has width dimension $W_2$ of about 0.5 µm×0.5 µm. The actuator 820 may be mounted to a substrate material 830 such as, for example, glass or Silicone (Si). The electrode member 818 may have a width dimension $W_3$ of about 10 nm and a height $T_6$ of about 5 nm. A total length of the device 800 may be in the range of about 1 µm to about 2 µm.

Figure 9:
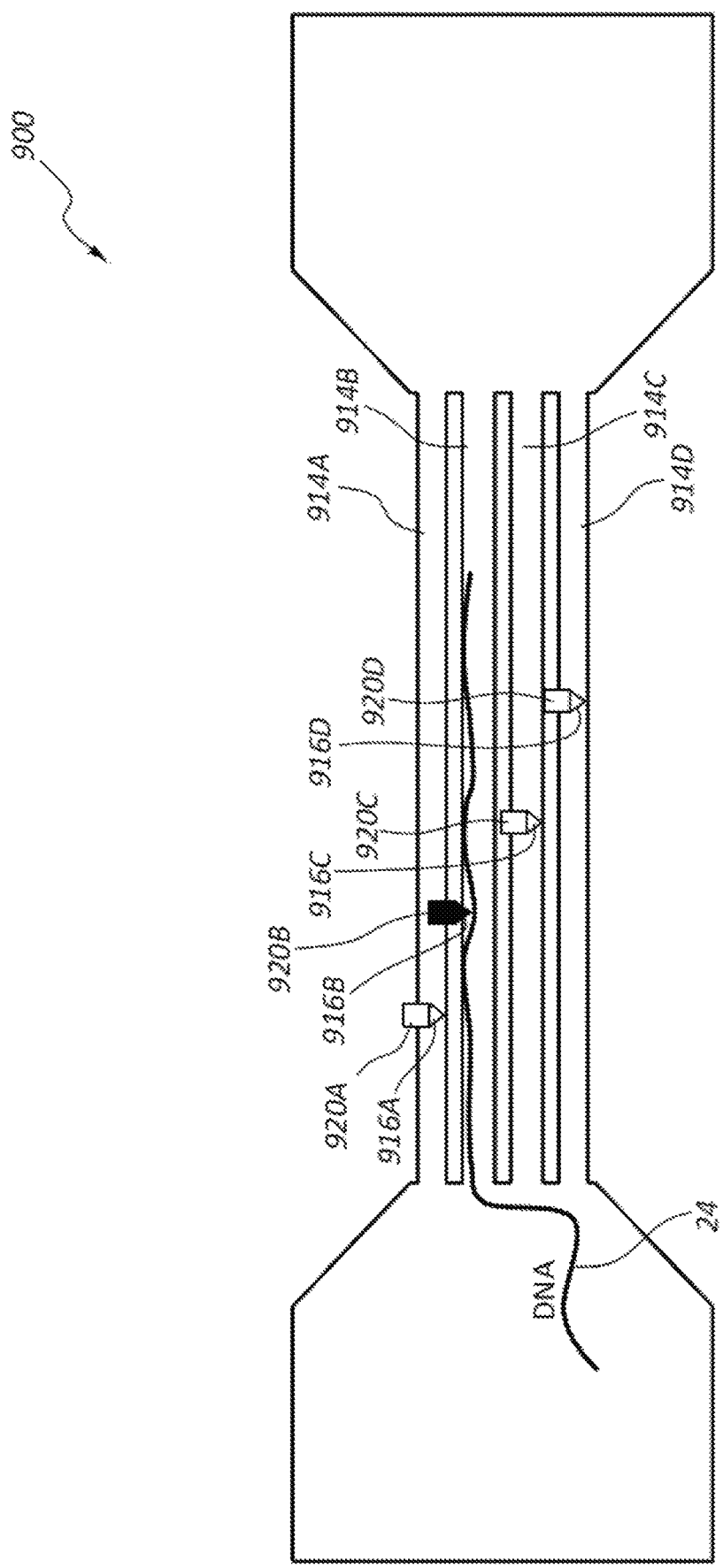
FIG. 9 schematically illustrates an example DNA sequencing device having a plurality of parallel nanochannels, at least some of which have adjustable electrode gap size in accordance with the present disclosure.

FIG. 9 illustrates another DNA sequencing device 900 having a single electrodes 916A-D (e.g., electrode probes) for each of a plurality of nanochannels 914A-D of the device. The electrodes 916A-D may be movable relative to respective nanochannels 914A-D. The electrodes 916A-D may be movable by operation of respective actuators 920A-D. The electrodes 916A-D may be movable into and out of positions in which the electrodes 916A-D block flow of DNA strands through the respective nanochannels 914A-D. By having one of a plurality of nanochannels 914 opened at a time, an operator can control which nanochannel 914A-D a DNA strand 24 runs through. A single one of the electrodes 916A-D (e.g., each electrode 916A-D including a pair of electrode members arranged on opposite sides of the respective nanochannel 914A-D) may be used to sense and sequence the DNA strand 24 as it translated through the selected open nanochannel 914A-D. The arrangement of DNA sequencing device 900 may allow many nanochannels to be available, and as one fails due to clogging or other damage, other nanochannels can be opened for passing DNA strands. It may be possible to include hundreds, thousands or order of magnitudes more of nanochannels in a given device 900. The device 900 may be configured to provide sequencing of multiple DNA strands 24 concurrently.

The multiple channel approach disclosed with reference to FIG. 9 permits the DNA strands 24 to run though the device in parallel. The oversampled information collected using device 900 may be used to increase signal-to-noise ratio (SNR) while still achieving high throughput. For example, if the same DNA sequence is included for all DNA strands 24 running though the channels 914, then multiple DNA samples can be read in parallel without impacting throughput, while still increasing SNR. The device 900 may also permit many different DNA samples, each with different sequences, to be evaluated at one time, thereby increase throughput. In some embodiments, there may be significant numbers of channels 914 that are formed in device 900 using, for example, an imprint method. Accordingly, a large number of channels may be available to concurrent sequencing of different DNA strands 24. One of the complexities of device 900 may involve making the master template that is used for imprinting these features, or using other fabrication methods to create the channel 914. Further, the electronics will require many parallel paths that are interconnected.

Figure 10:
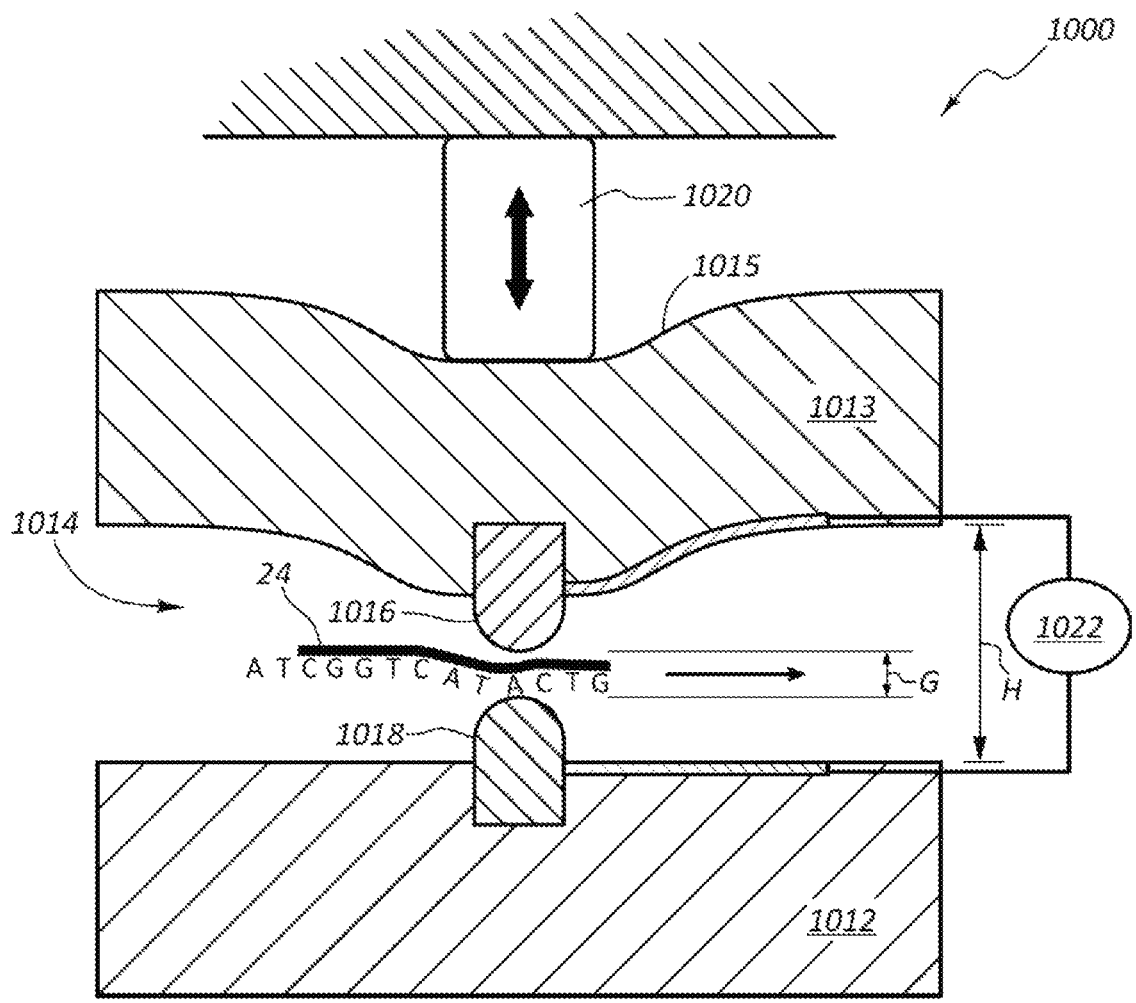
FIG. 10 schematically illustrates an example DNA sequencing device having an externally positioned actuating member to adjust an electrode gap size in accordance with the present disclosure.

FIG. 10 illustrates a DNA sequencing device 1000 that includes an actuator 1020 positioned outside of material 1013 of the device 1000. A first or top electrode member 1016 is provided as a probe that is positioned on the same side of the nanochannel 1014 as the actuator 1020. The second or bottom electrode member 1018 is positioned on a side of the nanochannel 1014 opposite the location of the actuator 1020 and also has a probe shape. In the ON state, the actuator 1020 applies a force to the material 1013, thereby causing the electrode member 1016 along the Z direction to narrow the gap G to a desired size. The actuator may include any of the actuator types described above, such as a heating element, a piezoelectric element, an electrostatic element, or the like. In another embodiment, the actuator 1020 may include an external laser to heat up the material 1013 or material of the actuator 1020 to provide the movement of material 1013 needed to change the size of gap G. The material 1013 may rebound or otherwise return to an original, undeformed position or shape upon deactivation of the actuator. The change in gap G will influence the tunneling current measured by the electrode members 1016, 1018 (e.g., using a controller or pre-amp 1022). In another variation of the device 1000, the bottom electrode member 1018 is formed as a layer (e.g., having a planar shape) rather than having a probe or relatively pointed shape as shown in FIG. 10.

Another approach for actuating one or more electrode members of a DNA sequencing device according to the present disclosure is to design the device with the electrode gap normally closed when the device is in the OFF state (e.g., before activating the actuator). When activated (e.g., the ON state), the electrode gap opens to a precisely controlled gap opening. In this method, an actuator for controlling the channel gap may include, for example, a cooling element. The cooling element may be controlled to cool the material in the region around one or more of the electrode members in order to contract the surrounding material. Contracting the surrounding material may then move one of the electrode members away from the other electrode member, thereby opening the electrode gap.

The mechanical actuation involved with opening the electrode gap from an initial closed position may be smaller than the amount of actuation required to reduce the gap according to the design of FIGS. 1-10. Since the final electrode gap opening is on the order of 0.3 nm to about 2 nm, and more particularly about 1 nm, the actuation is typically only a few nanometers total distance, or less, as compared to 5 nm to 10 nm of movement, or more, in the gap reduction designs of FIGS. 1-10.

Figure 11A:
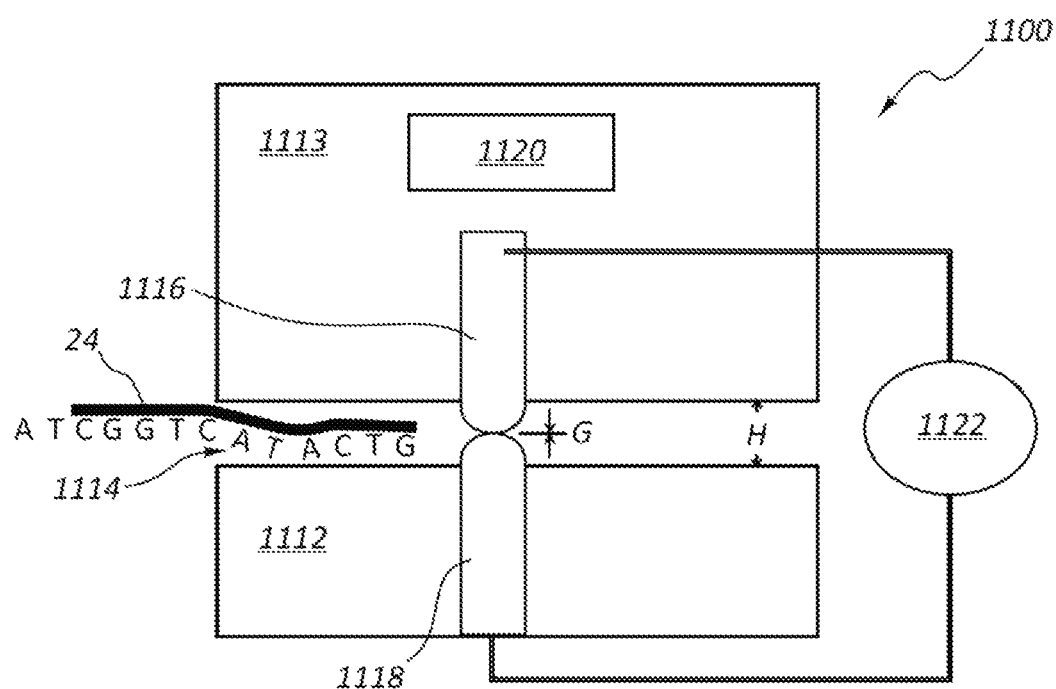
FIGS. 11A-11B schematically illustrate a nanofluidic DNA sequencing device in OFF and ON states, respectively, in accordance with the present disclosure.
Figure 11B:
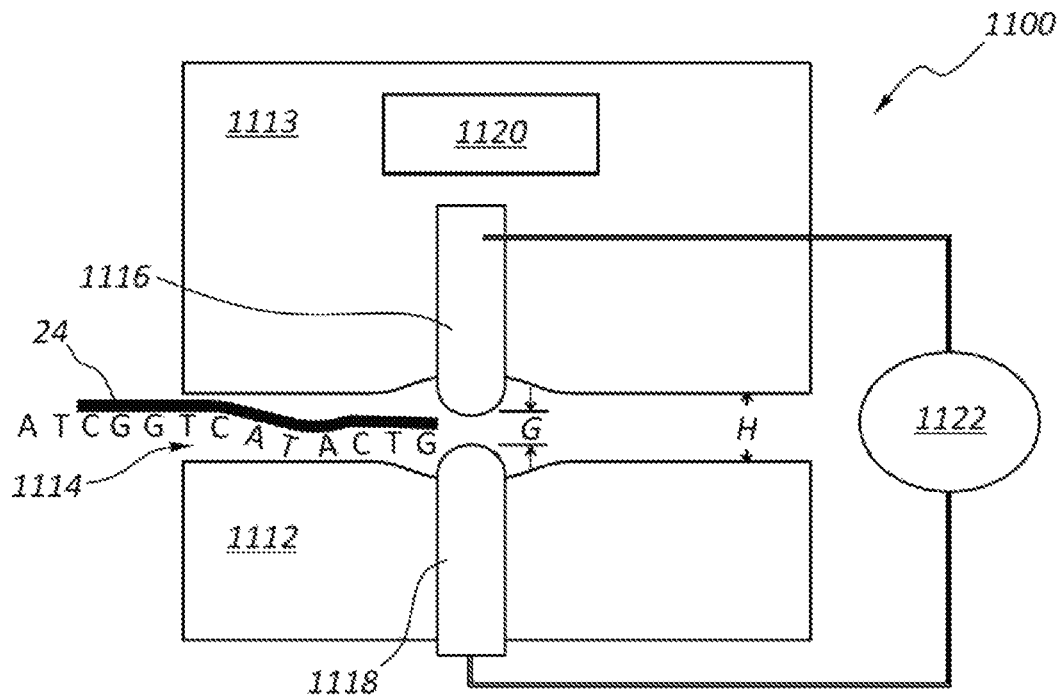

FIGS. 11A and 11B illustrate an embodiment of a DNA sequencing device 1100 that uses an actuator 1120 having a cooling element to move the electrode members 1116, 1118 (e.g., probes or electrodes) away from each other within the nanochannel 1114. Since the electrode gap G is controlled via cooling, the electrical signal-to-noise ratio (SNR) may improve with reduced thermal shot noise, and the DNA sample may be less prone to thermal damage. This active cooling method to open the electrode gap G may also make use of an additive process to form the one or both of the electrode members 1116, 1118 with a pointed or tapered end/tip. A pointed or tapered probe end/tip may assist with localizing the tunneling current to achieve higher discrimination of individual nucleotides (A,T,G,C) in a DNA strand.

The cooling element of the actuator 1120 may be or include a thermistor. The cooling element may include a metal having high thermal conductivity properties, and the cooling element may be attached to a thermistor that is located further from the probe region.

The cooling element of the actuator 1120 of FIGS. 11A and 11B may be embedded in a substrate material 1113. A first electrode member 1116 may also be embedded in or carried by the material 1113. A second electrode ember 1118 may be positioned in or carried by a substrate 1112 at a location opposite the first electrode member 1116. Portions of both electrode members 1116, 1118 are exposed within the nanochannel 1114. The electrode members 1116, 1118 are positioned in contact with each other when the device (e.g., actuator 1120) is in a rest state (e.g., the actuator 1120 is in an OFF state or is not yet activated). When the actuator 1120 is activated (e.g., turned ON or in an operating or activation state), the temperature of the material 1113 in the area of the actuator 1120 is cooled and constricts, thereby pulling the first electrode member 1116 away from the second electrode member 1118 to create a gap G. The gap G may be referred to as a restricted channel gap or an electrode gap.

The actuator 1120 may be controlled within the ON or operating state to apply more or less cooling in order to adjust the size of the gap G to a desired size. The desired size is typically in the range of about 0.3 nm to about 2 nm. Generally, the gap G is no greater than about 1 nm in order to provide desired accuracy and efficiency in measuring individual nucleotides (A,T,G,C) in a DNA strand passing through the nanochannel. The change in gap G will influence the tunneling current measured by the electrode members 1116, 1118 (e.g., using a controller or pre-amp 1122).

In some embodiments, the electrodes 1116 and/or 1118 may be movable to create a change in gap G in the range of about 0.3 nm to about 10 nm. The actuator 1120 may create a change in temperature of the material 1113 in the range of about 2° C. to about 50° C. In one example, the material of actuator 1120 comprises a polymer, a cured photo resist material, a nano-imprint material, or a spin on glass material. The material of actuator 1120 may, in at least one embodiment be in the range of about 1 um to about 100 um. In one embodiment, the actuator 1120 is formed using a spin coat process.

Figure 12:
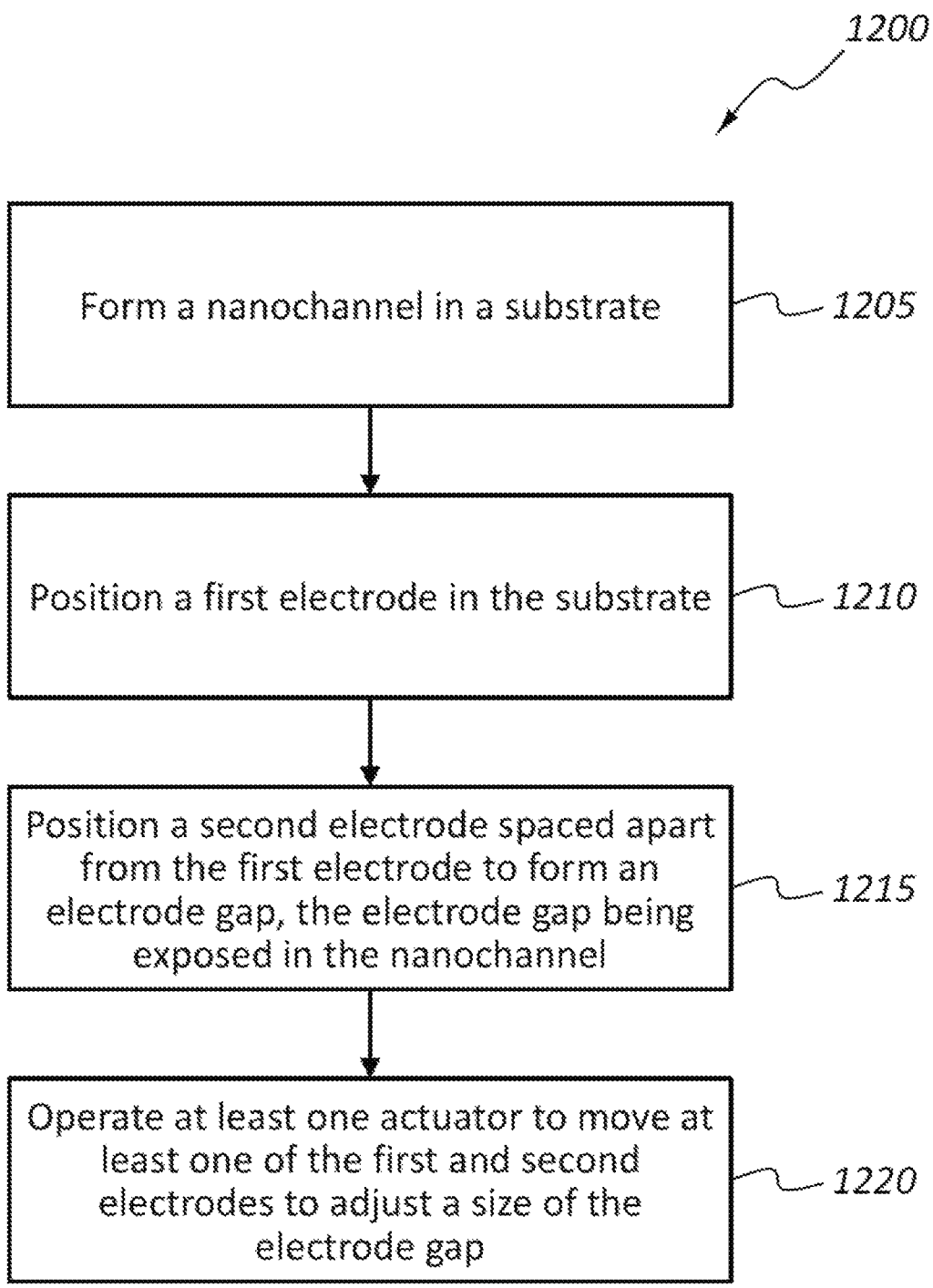
FIG. 12 is a flow diagram showing steps of an example method in accordance with the present disclosure.
Figure 13:
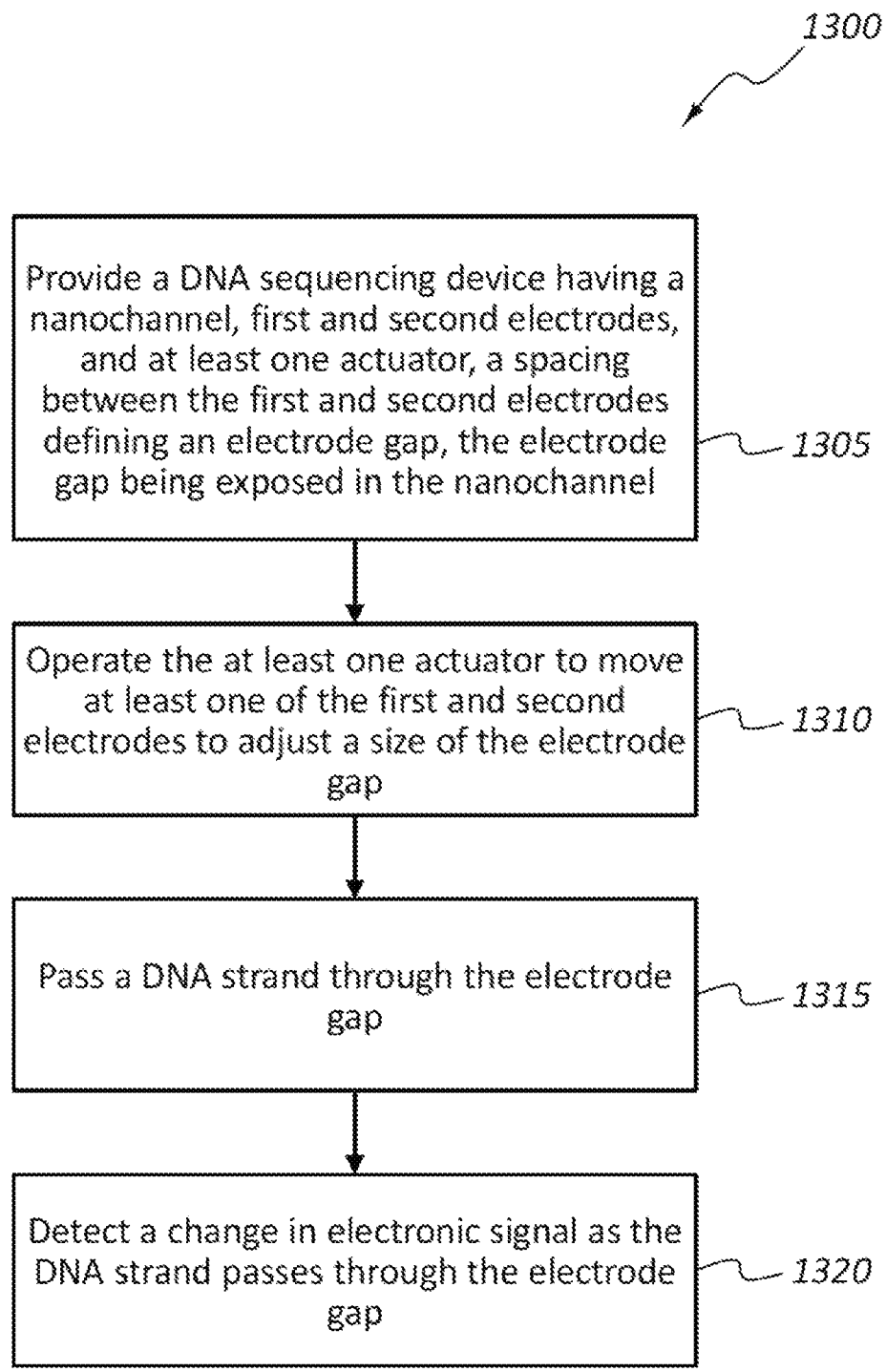
FIG. 13 is a flow diagram showing steps of another example method in accordance with the present disclosure.

FIGS. 12 and 13 are flow diagrams illustrating example methods associated with the DNA sequencing devices disclosed herein. FIG. 12 illustrates a method 1200 method of forming a DNA sequencing device. At block 1205, the method includes forming a nanochannel in a substrate. At block 1210, the method includes positioning a first electrode in the substrate. The method 1200 also includes positioning a second electrode spaced apart from the first electrode to form an electrode gap, the electrode gap being exposed in the nanochannel, as shown in block 1215. At block 1220, the method includes operating at least one actuator to move at least one of the first and second electrodes to adjust a size of the electrode gap.

The method 1200 may include, for example, positioning the at least one actuator in the substrate, or positioning a thermal conductor layer between the at least one actuator and at least one of the first and second electrodes. The at least one actuator may be one of a heating element, a piezoelectric or piezoceramic material, a cooling element, and an electrostatic member. The at least one actuator may include first and second actuators operable to separately move the first and second electrodes, respectively. The method may include providing a plurality of first electrodes and a plurality of second electrodes arranged to provide a plurality of electrode gaps that are each exposed within the nanochannel, and operating the at least one actuator moves at least one of the plurality of first electrodes and the plurality of second electrodes to adjust a size of the plurality of electrode gaps. The at least one actuator may include a separate actuator operable to move each of the first and second electrodes separately.

FIG. 13 illustrates a method 1300 of DNA sequencing. The method 1300 may include, at block 1305, providing a DNA sequencing device having a nanochannel, first and second electrodes, and at least one actuator, a spacing between the first and second electrodes defining an electrode gap, and the electrode gap being exposed in the nanochannel. The method 1300 also includes operating the at least one actuator to move at least one of the first and second electrodes to adjust a size of the electrode gap, passing a DNA strand through the electrode gap, and detecting a change in electronic signal as the DNA strand passes through the electrode gap. The detected change in electronic signal may be associated with one or more individual nucleotides of the DNA strand. The change in electronic signal may be used to determine a sequence of the nucleotides for the DNA strand.

The at least one actuator according to method 1300 may be fixed to the substrate. The electrode gap may initially be closed, and operating the at least one actuator may move the first and second electrodes away from each other to a provide a size for the electrode gap in the range of about 0.3 nm to about 2 nm. The electrode gap may initially be greater than 2 nm, and operating the at least one actuator may move the first and second electrodes toward each other to a provide a size for the electrode gap in the range of about 0.3 nm to about 2 nm.

The example methods 1200, 1300 may, in other embodiments, include fewer or additional steps that those illustrated in FIGS. 12 and 13. Further, many other methods and method steps may be possible based on the disclosures provided herein.

Figure 14:
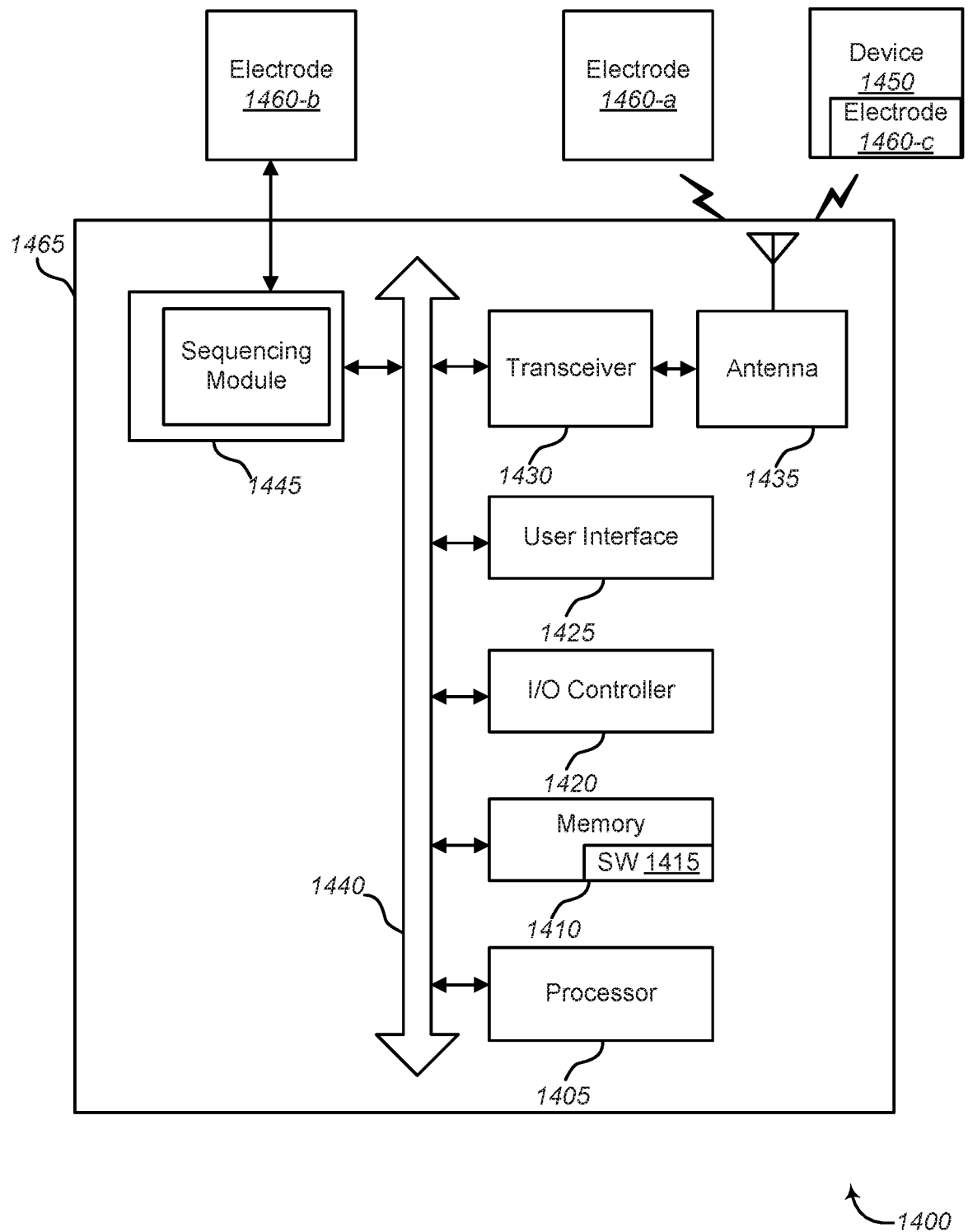
FIG. 14 shows a diagram of a system in accordance with various aspects of this disclosure.

FIG. 14 shows a system 1400 for use with the DNA sequencing devices and systems shown in FIGS. 1-10. System 1400 may include a control panel 1465. Control panel 1465 may be equivalent at least in part to a controller, control unit, processor or the like for use with the devices described above with reference to FIGS. 1-3. Control panel 1465 may include sequencing module 1445. The sequencing module 1445 may provide communications with one or more electrodes 1460 (also referred to as sensors or devices) directly or via other communication components, such as a transceiver 1430 and/or antenna 1435. The electrodes 1460 may represent one or more of the electrodes 16, 18, or pairs of such electrodes in any of the embodiments described above. The sequencing module 1445 may perform or control various operations associated with, for example, the electrodes 16, 18, actuator 20, controller 22, or other components of the DNA sequencing devices and related systems as described above with reference to FIGS. 1-10.

Control panel 1465 may also include a processor module 1405, and memory 1410 (including software/firmware code (SW) 1415), an input/output controller module 1420, a user interface module 1425, a transceiver module 1430, and one or more antennas 1435 each of which may communicate, directly or indirectly, with one another (e.g., via one or more buses 1440). The transceiver module 1430 may communicate bi-directionally, via the one or more antennas 1435, wired links, and/or wireless links, with one or more networks or remote devices. For example, the transceiver module 1430 may communicate bi-directionally with one or more of device 1450 and/or electrodes 1460-*a*, 1460-*c*. The device 1450 may be components of the DNA sequencing devices and related systems and devices described with reference to FIGS. 1-11, or other devices in communication with such systems and devices. The transceiver 1430 may include a modem to modulate the packets and provide the modulated packets to the one or more antennas 1435 for transmission, and to demodulate packets received from the one or more antennas 1435. In some embodiments (not shown) the transceiver may be communicate bi-directionally with one or more of device 1450, remote control device 1455, and/or electrodes 1460-*a*, 1460-*c* through a hardwired connection without necessarily using antenna 1435. While a control panel or a control device (e.g., 1405) may include a single antenna 1435, the control panel or the control device may also have multiple antennas 1435 capable of concurrently transmitting or receiving multiple wired and/or wireless transmissions. In some embodiments, one element of control panel 1465 (e.g., one or more antennas 1435, transceiver module 1430, etc.) may provide a connection using wireless techniques, including digital cellular telephone connection, Cellular Digital Packet Data (CDPD) connection, digital satellite data connection, and/or another connection.

The signals associated with system 1400 may include wireless communication signals such as radio frequency, electromagnetics, local area network (LAN), wide area network (WAN), virtual private network (VPN), wireless network (using 802.11, for example), 345 MHz, Z-WAVE®, cellular network (using 3G and/or LTE, for example), and/or other signals. The one or more antennas 1435 and/or transceiver module 1430 may include or be related to, but are not limited to, WWAN (GSM, CDMA, and WCDMA), WLAN (including BLUETOOTH® and Wi-Fi), WMAN (WiMAX), antennas for mobile communications, antennas for Wireless Personal Area Network (WPAN) applications (including RFID and UWB). In some embodiments, each antenna 1435 may receive signals or information specific and/or exclusive to itself. In other embodiments, each antenna 1435 may receive signals or information not specific or exclusive to itself.

In some embodiments, one or more electrodes 1460 (e.g., voltage, inductance, resistance, current, force, temperature, etc.) or devices 1450 may connect to some element of system 1400 via a network using one or more wired and/or wireless connections. In some embodiments, the user interface module 1425 may include an audio device, such as an external speaker system, an external display device such as a display screen, and/or an input device (e.g., remote control device interfaced with the user interface module 1425 directly and/or through I/O controller module 1420).

One or more buses 1440 may allow data communication between one or more elements of control panel 1465 (e.g., processor module 1405, memory 1410, I/O controller module 1420, user interface module 1425, etc.).

The memory 1410 may include random access memory (RAM), read only memory (ROM), flash RAM, and/or other types. The memory 1410 may store computer-readable, computer-executable software/firmware code 1415 including instructions that, when executed, cause the processor module 1405 to perform various functions described in this disclosure (e.g., initiating an adjustment of a lighting system, etc.). Alternatively, the software/firmware code 1415 may not be directly executable by the processor module 1405 but may cause a computer (e.g., when compiled and executed) to perform functions described herein. Alternatively, the computer-readable, computer-executable software/firmware code 1415 may not be directly executable by the processor module 1405 but may be configured to cause a computer (e.g., when compiled and executed) to perform functions described herein. The processor module 1405 may include an intelligent hardware device, e.g., a central processing unit (CPU), a microcontroller, an application-specific integrated circuit (ASIC), etc.

In some embodiments, the memory 1410 can contain, among other things, the Basic Input-Output system (BIOS) which may control basic hardware and/or software operation such as the interaction with peripheral components or devices. For example, the sequencing module 1445, and other modules and operational components of the control panel 1465 used to implement the present systems and methods may be stored within the system memory 1410. Applications resident with system 1400 are generally stored on and accessed via a non-transitory computer readable medium, such as a hard disk drive or other storage medium. Additionally, applications can be in the form of electronic signals modulated in accordance with the application and data communication technology when accessed via a network interface (e.g., transceiver module 1430, one or more antennas 1435, etc.).

Many other devices and/or subsystems may be connected to one or may be included as one or more elements of system 1400. In some embodiments, all of the elements shown in FIG. 14 need not be present to practice the present systems and methods. The devices and subsystems can be interconnected in different ways from that shown in FIG. 14. In some embodiments, an aspect of some operation of a system, such as that shown in FIG. 14, may be readily known in the art and are not discussed in detail in this application. Code to implement the present disclosure can be stored in a non-transitory computer-readable medium such as one or more of system memory 1410 or other memory. The operating system provided on I/O controller module 1420 may be iOS®, ANDROID®, MS-DOS®, MS-WINDOWS®, OS/2®, UNIX®, LINUX®, or another known operating system.

The transceiver module 1430 may include a modem configured to modulate the packets and provide the modulated packets to the antennas 1435 for transmission and/or to demodulate packets received from the antennas 1435. While the control panel or control device (e.g., 1405) may include a single antenna 1435, the control panel or control device (e.g., 1405) may have multiple antennas 1435 capable of concurrently transmitting and/or receiving multiple wireless transmissions.

In some embodiments, the DNA sequencing device and systems described herein may be used to collect electronic signals associated with the nucleotides of a DNA strand passing through the gap between electrode pairs, and the collected electronic signals are processed at a different location. The processing may include electronically comparing the collected electronic signals to ranges of electronic signals associated with specific nucleotide types which have been previously determined and stored. In other embodiments, the DNA sequencing device includes capability of processing the collected electronic signals, conducting such comparison evaluations, and even formulating an order or sequence for the nucleotides of the DNA strand being evaluated.

INCORPORATION BY REFERENCE

The entire content of each of the previously filed provisional patent applications listed below are incorporated by reference in their entireties into this document, as are the related non-provisional patent applications of the same title filed concurrently with the present application. If the same term is used in both this document and one or more of the incorporated documents, then it should be interpreted to have the broadest meaning imparted by any one or combination of these sources unless the term has been explicitly defined to have a different meaning in this document. If there is an inconsistency between any of the following documents and this document, then this document shall govern. The incorporated subject matter should not be used to limit or narrow the scope of the explicitly recited or depicted subject matter.

U.S. Prov. App. No. 62/453,270, titled "SINGLE-MOLECULE DNA SEQUENCING METHOD USING CONFINED NANO-FLUIDIC CHANNEL AND SUB-NANOMETER ELECTRODE GAP," filed on 1 Feb. 2017, and U.S. patent application Ser. No. 15/886,442, titled "SINGLE-MOLECULE DNA SEQUENCING METHOD USING CONFINED NANO-FLUIDIC CHANNEL AND SUB-NANOMETER ELECTRODE GAP," filed on 1 Feb. 2018.

U.S. Prov. App. No. 62/453,298, titled "FABRICATION OF NANOCHANNEL WITH INTEGRATED ELECTRODES FOR DNA SEQUENCING USING TUNNELING CURRENT," filed on 1 Feb. 2017, and U.S. patent application Ser. No. 15/886,511, titled "FABRICATION OF NANOCHANNEL WITH INTEGRATED ELECTRODES FOR DNA SEQUENCING USING TUNNELING CURRENT," filed on 1 Feb. 2018.

U.S. Prov. App. No. 62/453,307, titled "METHOD TO FABRICATE A NANOCHANNEL FOR DNA SEQUENCING BASED ON NARROW TRENCH PATTERNING PROCESS," filed on 1 Feb. 2017, and U.S. patent application Ser. No. 15/886,533, titled "METHOD TO FABRICATE A NANOCHANNEL FOR DNA SEQUENCING BASED ON NARROW TRENCH PATTERNING PROCESS," filed on 1 Feb. 2018.

U.S. Prov. App. No. 62/453,323, titled "FABRICATION OF A DEVICE FOR SINGLE-MOLECULE DNA SEQUENCING USING SIDEWALL LITHOGRAPHY," filed on 1 Feb. 2017, and U.S. patent application Ser. No. 15/886,560, titled "FABRICATION OF A DEVICE FOR SINGLE-MOLECULE DNA SEQUENCING USING SIDEWALL LITHOGRAPHY," filed on 1 Feb. 2018.

U.S. Prov. App. No. 62/453,339, titled "FABRICATION OF A NANOCHANNEL FOR DNA SEQUENCING USING ELECTRICAL PLATING TO ACHIEVE TUNNELING ELECTRODE GAP," filed on 1 Feb. 2017, and U.S. patent application Ser. No. 15/886,581, titled "FABRICATION OF A NANOCHANNEL FOR DNA SEQUENCING USING ELECTRICAL PLATING TO ACHIEVE TUNNELING ELECTRODE GAP," filed on 1 Feb. 2018.

U.S. Prov. App. No. 62/453,346, titled "NANOSTRUCTURES TO CONTROL DNA STRAND ORIENTATION AND POSITION LOCATION FOR TRANSVERSE DNA SEQUENCING," filed on 1 Feb. 2017, and U.S. patent application Ser. No. 15/886,608, titled "NANOSTRUCTURES TO CONTROL DNA STRAND ORIENTATION AND POSITION LOCATION FOR TRANSVERSE DNA SEQUENCING," filed on 1 Feb. 2018.

U.S. Prov. App. No. 62/453,365, titled "FABRICATION OF WEDGE SHAPED ELECTRODE FOR ENHANCED DNA SEQUENCING USING TUNNELING CURRENT," filed on 1 Feb. 2017, and U.S. patent application Ser. No. 15/886,661, titled "FABRICATION OF WEDGE SHAPED ELECTRODE FOR ENHANCED DNA SEQUENCING USING TUNNELING CURRENT," filed on 1 Feb. 2018.

U.S. Prov. App. No. 62/453,329, titled "DIRECT SEQUENCING DEVICE WITH A TOP-BOTTOM ELECTRODE PAIR," filed on 1 Feb. 2017, and U.S. patent application Ser. No. 15/886,685, titled "DIRECT SEQUENCING DEVICE WITH A TOP-BOTTOM ELECTRODE PAIR," filed on 1 Feb. 2018.

U.S. Prov. App. No. 62/453,376, titled "MICRO AND NANOFLUIDIC CHANNEL CONTROLLED ACTUATION TO OPEN CHANNEL GAP," filed on 1 Feb. 2017.

U.S. Prov. App. No. 62/469,393, titled "METHOD TO AMPLIFY TRANSVERSE TUNNELING CURRENT DISCRIMINATION OF DNA NUCLEOTIDES VIA NUCLEOTIDE SITE SPECIFIC ATTACHMENT OF DYE-PEPTIDE," filed on 9 Mar. 2017, and U.S. patent application Ser. No. 15/886,736, titled "METHOD TO AMPLIFY TRANSVERSE TUNNELING CURRENT DISCRIMINATION OF DNA NUCLEOTIDES VIA NUCLEOTIDE SITE SPECIFIC ATTACHMENT OF DYE-PEPTIDE," filed on 9 Mar. 2018.

U.S. Prov. App. No. 62/469,409, titled "VERTICAL NANOPORE COUPLED WITH A PAIR OF TRANSVERSE ELECTRODES HAVING A UNIFORM ULTRASMALL NANOGAP FOR DNA SEQUENCING," filed on 9 Mar.

2017, and U.S. patent application Ser. No. 15/886,723, titled "VERTICAL NANOPORE COUPLED WITH A PAIR OF TRANSVERSE ELECTRODES HAVING A UNIFORM ULTRASMALL NANOGAP FOR DNA SEQUENCING," filed on 9 Mar. 2018.

The detailed description set forth above in connection with the appended drawings describes examples and does not represent the only instances that may be implemented or that are within the scope of the claims. The terms "example" and "exemplary," when used in this description, mean "serving as an example, instance, or illustration," and not "preferred" or "advantageous over other examples." The detailed description includes specific details for the purpose of providing an understanding of the described techniques. These techniques, however, may be practiced without these specific details. In some instances, known structures and apparatuses are shown in block diagram form in order to avoid obscuring the concepts of the described examples.

In addition, any disclosure of components contained within other components or separate from other components should be considered exemplary because multiple other architectures may potentially be implemented to achieve the same functionality, including incorporating all, most, and/or some elements as part of one or more unitary structures and/or separate structures.

The previous description of the disclosure is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not to be limited to the examples and designs described herein but is to be accorded the broadest scope consistent with the principles and novel features disclosed.

The process parameters, actions, and steps described and/or illustrated in this disclosure are given by way of example only and can be varied as desired. For example, while the steps illustrated and/or described may be shown or discussed in a particular order, these steps do not necessarily need to be performed in the order illustrated or discussed. The various exemplary methods described and/or illustrated here may also omit one or more of the steps described or illustrated here or include additional steps in addition to those disclosed.

This description, for purposes of explanation, has been described with reference to specific embodiments. The illustrative discussions above, however, are not intended to be exhaustive or limit the present systems and methods to the precise forms discussed. Many modifications and variations are possible in view of the above teachings. The embodiments were chosen and described in order to explain the principles of the present systems and methods and their practical applications, to enable others skilled in the art to utilize the present systems, apparatus, and methods and various embodiments with various modifications as may be suited to the particular use contemplated.

What is claimed is:

1. A DNA sequencing device, comprising: a substrate; a nanochannel formed in the substrate; a first electrode; a second electrode arranged opposite the first electrode, a distance between the first and second electrodes defining an electrode gap that is exposed within the nanochannel; at least one actuator operable to move at least one of the first and second electrodes to adjust a size of the electrode gap; and a thermal conductor layer positioned between the at least one actuator and at least one of the first and second electrodes.

2. The device of claim 1, wherein the first electrode is arranged parallel with the nanochannel and the second electrode is arranged perpendicular to the first electrode.

3. The device of claim 1, wherein the second electrode is positioned in the substrate.

4. The device of claim 1, wherein the size of the electrode gap after adjustment by the at least one actuator is in the range of about 0.3 nm to about 2 nm.

5. The device of claim 1, wherein the at least one actuator comprises at least one of a heating element, a piezoelectric or piezoceramic material, a cooling element, and an electrostatic member.

6. The device of claim 1, wherein the at least one actuator comprises first and second actuators operable to separately move the first and second electrodes, respectively.

7. The device of claim 1, wherein the thermal conductor layer positioned in the substrate between the at least one actuator and at least one of the first and second electrodes.

8. The device of claim 1, wherein the at least one actuator is embedded in the substrate.

9. The device of claim 1, further comprising a plurality of first electrodes and a plurality of second electrodes arranged to provide a plurality of electrode gaps that are each exposed within the nanochannel, and the at least one actuator is operable to move at least one of the plurality of first electrodes and the plurality of second electrodes to adjust the size of the plurality of electrode gaps.

10. A method of forming a DNA sequencing device, the method comprising: forming a nanochannel in a substrate; positioning a first electrode in the substrate; positioning a second electrode spaced apart from the first electrode to form an electrode gap, the electrode gap being exposed in the nanochannel; operating at least one actuator to move at least one of the first and second electrodes to adjust a size of the electrode gap; and positioning a thermal conductor layer between the at least one actuator and at least one of the first and second electrodes.

11. The method of claim 10, further comprising positioning the at least one actuator in the substrate.

12. The method of claim 10, wherein the at least one actuator is one of a heating element, a piezoelectric or piezoceramic material, a cooling element, and an electrostatic member.

13. The method of claim 12, wherein the at least one actuator comprises first and second actuators operable to separately move the first and second electrodes, respectively.

14. The method of claim 10, further comprising providing a plurality of first electrodes and a plurality of second electrodes arranged to provide a plurality of electrode gaps that are each exposed within the nanochannel, and operating the at least one actuator moves at least one of the plurality of first electrodes and the plurality of second electrodes to adjust a size of the plurality of electrode gaps.

15. The method of claim 10, wherein the at least one actuator includes a separate actuator operable to move each of the first and second electrodes separately.

16. A method of DNA sequencing, the method comprising: providing a DNA sequencing device having a nanochannel, first and second electrodes, and at least one actuator, a spacing between the first and second electrodes defining an electrode gap, the electrode gap being exposed in the nanochannel, and a thermal conductor layer positioned between the at least one actuator and at least one of the first and second electrodes; operating the at least one actuator to move at least one of the first and second electrodes to adjust a size of the electrode gap; passing a DNA strand through the electrode gap; detecting a change in electronic signal as the DNA strand passes through the electrode gap.

17. The method of claim 16, wherein the at least one actuator is fixed to a substrate, the nanochannel being formed at least in part in the substrate.

18. The method of claim 16, wherein the electrode gap is initially closed, and operating the at least one actuator moves the first and second electrodes away from each other to a provide a size for the electrode gap in the range of about 0.3 nm to about 2 nm.

19. The method of claim 16, wherein the electrode gap is initially greater than 2 nm, and operating the at least one actuator moves the first and second electrodes toward each other to a provide a size for the electrode gap in the range of about 0.3 nm to about 2 nm.

\* \* \* \* \*